US006864286B2

(12) United States Patent
Uckun et al.

(10) Patent No.: US 6,864,286 B2
(45) Date of Patent: Mar. 8, 2005

(54) INHIBITORS OF THE EGF-RECEPTOR TYROSINE KINASE AND METHODS FOR THEIR USE

(75) Inventors: Fatih M. Uckun, White Bear Lake, MN (US); Yaguo Zheng, New Brighton, MN (US); Sutapa Ghosh, Shoreview, MN (US)

(73) Assignee: Parker Hughes Institute, St. Paul, MN (US)

( * ) Notice: Subject to any disclaimer, the term of this patent is extended or adjusted under 35 U.S.C. 154(b) by 425 days.

(21) Appl. No.: 09/947,862

(22) Filed: Sep. 5, 2001

(65) Prior Publication Data

US 2002/0107284 A1 Aug. 8, 2002

Related U.S. Application Data

(63) Continuation of application No. 09/273,002, filed on Mar. 19, 1999, now Pat. No. 6,355,678.
(60) Provisional application No. 60/090,998, filed on Jun. 29, 1998, and provisional application No. 60/097,361, filed on Aug. 21, 1998.

(51) Int. Cl.[7] ...................... A61K 31/277; C07C 255/07
(52) U.S. Cl. ...................................... 514/521; 558/305
(58) Field of Search .......................... 514/521; 558/305

(56) References Cited

U.S. PATENT DOCUMENTS

| | | | |
|---|---|---|---|
| 4,061,767 A | 12/1977 | Ertel et al. | |
| 4,346,097 A | 8/1982 | Schweiss et al. | |
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,240,960 A | 8/1993 | Hambleton et al. | |
| 5,532,259 A | 7/1996 | Bartlett et al. | |
| 5,747,664 A | 5/1998 | Schleyerbach et al. | |
| 5,780,592 A | 7/1998 | Mullner et al. | |
| 5,977,151 A | 11/1999 | Mullner et al. | |
| 6,218,388 B1 | 4/2001 | Boschelli et al. | |

FOREIGN PATENT DOCUMENTS

| | | |
|---|---|---|
| DE | 196 10 955 A1 | 9/1997 |
| GB | 1 571 990 | 7/1980 |
| WO | WO 94/24095 | 10/1994 |

OTHER PUBLICATIONS

Abrams, M.D., J. S. et al., "New Chemotherapeutic Agents for Breast Cancer", *Cancer*, vol. 74, No. 3, pp. 1164–1176 (Aug. 1, 1994).

Bacon, D. J. et al., "A Fast Algorithm for Rendering Space–Filling Molecule Pictures", *J. Molec. Graphics*, vol. 6, No. 4, pp. 219–220 (Dec. 1988).

Bertolini, G., et al., "A New Rational Hypothesis for the Pharmacophore of the Active Metabolite of Leflunomide, a Potent Immunosuppressive Drug", *J. Med. Chem*, vol. 40, No. 13, pp. 2011–2016 (Jun. 20, 1997).

Bohm, H. J., "LUDI: Rule–Based Automatic Design of New Substituents for Enzyme Inhibitor Leads",*J. Comput. Aided Mol. Des.*, vol. 6, No. 6, pp. 593–606 (Dec. 1992).

Bohm, H. J., "The Development of a Simple Empirical Scoring Function to Estimate the Binding Constant for a Protein–Ligand Complex of Known Three–Dimensional Structure",*J. Comput. Aided Mol. Des.*, vol. 8, No. 3, pp. 243–256 (Jun. 1994).

Chrysogelos, S.A. et al., "EGF Receptor Expression, Regulation, and Function in Breast Cancer", *Breast Cancer Res.Treat.*, vol. 29, pp. 29–40 (1994).

Connolly, M. L., "Solvent–Accessible Surfaces of Proteins and Nucleic Acids", *Science*, vol. 221, pp. 709–713 (Aug. 19, 1983).

Courville, P. et al., "Pseudoepitheliomatous Hyperplasia in Cutaneous Tcell Lymphoma. A Clinical, Histopathological and Immunohistochemical Study with Particular Interest in Epithelial Growth Factor Expression",*British Journal of Dermatology*, vol. 140, No. 3, pp. 421–426 (Mar. 1999).

De Luca, A. et al., "Detection of Circulating Tumor Cells in Carcinoma Patients by a Novel Epidermal Growth Factor Receptor Reverse Transcription–PCR Assay", *Clin. CancerRes.*, vol. 6, No. 4, pp. 1439–1444 (Apr. 2000) (Abstract Only).

Fox, S.B, et al., "The Epidermal Growth Factor Receptor as a Prognostic Marker: Results of 370 Patients and Review of 3009 Patients", *Breast Cancer Res.Treat.*, vol. 29, pp. 41–49 (1994).

Fry, D. W. et al., "Inhibitors of Protein Tyrosine Kinases", *Curr. Opin. Biotechnol*, vol. 6, No. 1, pp. 662–667 (Feb. 1995).

George–Nascimento et al., "Characterization of Recombinant Human Epidermal Growth Factor Produced in Yeast", *Biochemistry*, vol. 27, pp. 797–802 (1988).

Ghosh, S. et al., "α–Cyano–β–hydroxy–β–methyl–N–[4–(trifluoromethoxy)phenyl] Propenamide: An Inhibitor of the Epidermal Growth Factor Receptor Tyrosine Kinase with Potent Cytotoxic Activity against Breast Cancer Cells", *Clinical Cancer Research*, vol. 4, pp. 2657–2668 (Nov. 1998).

(List continued on next page.)

*Primary Examiner*—Taofiq Solola
(74) *Attorney, Agent, or Firm*—Merchant & Gould P.C.

(57) ABSTRACT

Novel compounds and pharmaceutical compositions useful as EGFR tyrosine kinase inhibitors. Methods of the invention include administration of the EGFR TK inhibitors to treat diseases characterized by enhanced expression of EGF, including cancers, particularly breast cancer. Additionally, a homology model representing the structure of EGFR kinase domain is provided, which model is useful for the rationally design and screening of compounds predicted to bind favorably to EGFR and to inhibit EGFR TK.

3 Claims, 15 Drawing Sheets

OTHER PUBLICATIONS

Goodman, P. A. et al., "Role of Tyrosine Kinases in Induction of c–jun Proto–oncogene in Irradiated B–lineage Lymphoid Cells", vol. 273, No. 28, pp. 17742–17748 (Jul. 10, 1998).

Gusterson, B. et al., "Cellular Localisation of Human Epidermal Growth Factor Receptor", *Cell Biology International Reports*, vol. 8, No. 8, pp. 649–658 (Aug. 1984).

Hermanson, et al., *Bioconjugate Techniques*, Academic Press, 1996.

Hermanson, et al., *Immobilized Affinity Ligand Techniques*, Academic Press, 1992.

Hubbard, S. R., "Crystal Structure of the Activated Insulin Receptor Tyrosine Kinase in Complex with Peptide Substrate and ATP Analog", *The E.M.B.O. Journal*, vol. 16, No. 18, pp. 5572–5581 (1997).

Khazale, K. et al., "EGF Receptor in Neoplasia and Metastatis", *Cancer & Metasis Reviews*, vol. 12, pp. 255–274 (1993).

Kraulis, P.J., "MOLSCRIPT: A Program to Produce Both Detailed and Schematic Plots of Protein Structures",*J. Appl. Cryst*, vol. 24, pp. 946–950 (Oct. 1, 1991).

Kuntz, I. D. et al., "A Geometric Approach to Macromolecule–Ligand Interactions", *J. Mol. Biol.*, vol. 161, No. 1, pp. 269–288 (Oct. 25, 1982).

Kuo, E. A. et al., "Synthesis, Structure–Activity Relationships, and Pharmacokinetic Properties of Dihydroorotate Dehydrogenase Inhibitors: 2–Cyano–3–cyclopropyl–3–hydroxy–N–[3'–methyl–4'–(trifluoromethyl)phenyl]propenamide and Related Compounds", *J. Med. Chem.*, vol. 39, No. 23, pp. 4608–4621 (Nov. 8, 1996).

Mahajan, S. et al., Rational Design and Synthesis of a Novel Anti–leukemic Agent Targeting Bruton's Tyrosine Kinase (BTK), LFM–A13 [α–Cyano–β–Hydroxy–62 –Methyl–N–(2,5–Dibromophenyl)Propenamide],*J. Biol. Chem.*, vol. 274, No. 14, pp. 9587–9599 (Apr. 2, 1999).

Mahajan, S. et al., "Src Family Protein Tyrosine Kinases Induce Autoactivation of Bruton's Tyrosine Kinase",*Mol. Cell. Biol.*, vol. 15, No. 10, pp. 5304–5311 (Oct. 1995).

Mattar, T. et al., "Inhibition of the Epidermal Growth Factor Receptor Tyrosine Kinase Activity by Leflunomide" *FEBS Lett.*, vol. 334, No. 2, pp. 161–164 (Nov. 1993).

Mendelsohn, J. et al., "Antibodies to Growth Factors and Receptors", *Biologic Therapy of Cancer*2nd Edition, pp. 607–623 (1995).

Merritt, E. et al.,"Raster3D 2.0 A Program for Photorealistic Molecular Graphics", *Acta Cryst*, vol. D50, Part 6, pp. 869–873 (Nov. 1, 1994).

Mirmohammadsadegh, A, et al., "Differential Modulation of Pro– and Antiinflammatory Cytokine Receptors by N–(4–trifluoromethylphenyl)–2–cyano–3–hydroxy–crotonic acid amide(A77 1726), The Physiologically Active Metabolite of the Novel Immunomodulator Leflunomide", Chemical Abstracts, vol. 129, No. 3, one page (Jul. 20, 1998).

Mohammadi, M. et al., "Structure of the FGF Receptor Tyrosine Kinase Domain Reveals a Novel Autoinhibitory Mechanism", *Cell*, vol. 86, pp. 577–587 (Aug. 23, 1996).

Mohammadi, M. et al., "Structures of the Tyrosine Kinase Domain of Fibroblast Growth Factor Receptor in Complex with Inhibitors", *Science*, vol. 276, No. 5314, pp. 955960 (May 9, 1997).

Moyer, J. D. et al., "Induction of Apoptosis and Cell Cycle Arrest by CP–358,774, an Inhibitor of Epidermal Growth Factor Receptor Tyrosine Kinase", *Cancer Res.*, vol. 57, No. 21, pp. 4838–4848 (Nov. 1, 1997).

Nakamura, N. et al., "An Epidermal Growth Factor Receptor/Jak2 Tyrosine Kinase Domain Chimera Induces Tyrosine Phosphorylation of Stat5 and Transduces a Growth Signal in Hematopoietic Cells", *J. Biol. Chem.*, vol. 271, No. 32, pp. 19483–19488 (Aug. 9, 1996) (Abstract Only).

Naria, R. K. et al., "4–(3–40 – Bromo–4'hydroxylphenyl)–amino–6,7–dimethoxyquinazoline: A Novel Quinazoline Derivative with Potent Cytotoxic Activity against Human Glioblastoma Cells", *Clin., Can. Res.*, vol. 4, No. 6, pp. 1405–1414 (Jun. 1998).

Palmer, B. D. et al., "Tyrosine Kinase Inhibitors. 11. Soluble Analogues of Pyrroto–and Pyrazoloquinazolines as Epidermal Growth Factor Receptor Inhibitors: Synthesis, Biological Evaluation, and Modeling of the Mode of Binding", *J. Med. Chem.*, vol. 40, pp. 1519–1529 (1997).

Parnham, M. J., "Leflynomide: A Potential New Disease-–Modifying AntiRheumatic Drug", *Exp. Opin Invest. Drugs*, vol. 4, No. 8, pp. 777–779 (Aug. 1900).

Patterson, J. et al., "3–carboxy–5–methyl–N–[4–(trifluoromethyl) phenyl]–4–isoxazolecarboxamide, New Prodrug For The Antiarthritic Agent 2–cyano–3–hydroxy–N–[4–(trifluoromethyl) phenyl]–2–butenamide", Chemical Abstracts, vol. 116, No. 9, one page (Mar. 2, 1992).

Real, F. et al., "Expression of Epidermal Growth Factor Receptor in Human Cultured Cells and Tissues: Relationship to Cell Lineage and Stage of Differentiation", *Cancer Research*, vol. 46, No. 9, pp. 47264731 (Sep. 1986).

Saouaf, S. J. et al., "Reconstitution of the B Cell Antigen Receptor Signaling Components in COS Cells", *J. Biol. Chem.*, vol. 270, No. 45, pp. 27072–27078 (Nov. 10, 1995).

Shibuya, H. et al., "IL–2 and EGF Receptors Stimulate the Hematopoietic Cell Cycle via Different Signaling Pathways: Demonstration of a Novel Role for cmyc", *Cell*, vol. 70, No. 1, pp. 57–67 (Jul. 10, 1992) (Abstract Only).

Sicheri, F. et al., "Crystal Structure of the Src Family Tyrosine Kinase Hck", *Nature*, vol. 385, pp. 602–609 (Feb. 13, 1997).

Sjogren, E. B. et al., "Synthesis and Biological Activity of a Series of Diaryl–Substituted αCyano–β–hydroxypropenamides, a New Class of Anthelmintic Agents",*J. Med. Chem.*, vol. 34, No. 11, pp. 3295–3301 (Nov. 1991).

Sudbec, E. et al., "Structure–based Design of Specific Inhibitors of Janus Kinase 3 as Apoptosis–inducing Anti-leukemic Agents", *Clin. Can. Res.*, vol. 5, No. 6, pp. 1569–1582 (Jun. 1999).

Takahashi, T. et al., "A Potential Molecular Approach to ex vivo Hematopoietic Expansion with Recombinant Epidermal Growth Factor Receptor–Expressing Adenovirus Vector", *Blood*, vol. 91, No. 12, pp. 45094515 (Jun. 15, 1998) (Abstract Only).

Toi, M. et al., "Epidermal Growth Factor Receptor Expression as a Prognostic Indicator in Breast Cancer", *European J. Cancer*, vol. 27, No. 8, pp. 977–980 (Aug. 1991).

Uckun, F. M. et al., "Biotherapy of B–Cell Precursor Leukemia by Targeting Genistein to CD19–Associated Tyrosine Kinases", *Science*, vol. 267, No. 5199, pp. 886–891 (Feb. 10, 1995).

Uckun, F.M. et al., "BTK as a Mediator of Radiation–Induced Apoptosis in DT–40 Lymphoma B Cells", *Science* vol. 273, pp. 1096–1100 (Aug. 23, 1996).

Uckun, F. M. et al., "Cytotoxic Activity of Epidermal Growth Factor–Genistein Against Breast Cancer Cells", *Clin. Can. Res.*, vol. 4, No. 4, pp. 901–912 (Apr. 1998).

Vassilev, A. et al., "Buton's Tyrosine Kinase as an Inhibitor of the Fas/CD95 Death–inducing Signaling Complex", *J. Biol. Chem.*, vol. 274, No. 3, pp. 1646–1656 (Jan. 15, 1999).

Wakeling, A. E. et al., "Specific Inhibition of Epidermal Growth Factor Receptor Tyrosine Kinase by 4–Anilinoquinazolines", *Breast Cancer Research & Treatment*, vol. 38, pp. 67–73 (1996).

Xu, X. et al., "Inhibition of Protein Tyrosine Phosphorylation in T Cells by a Novel Immunosuppressive Agent, Leflunomide", *Journal of Biological Chemistry*, vol. 270, No. 21, pp. 12398–12403 (May 26, 1995).

Xu, X. et al., "Two Activities of the Immunosuppressive Metabolite of Leflunomide, A77 1726. Inhibition of Pyrimidine nucleotide Synthesis and Protein Tyrosine Phosphorylation", Chemical Abstracts, vol. 125, No. 15, one page (Oct. 7, 1996).

Xu, X. et al., "Two Activities of the Immunosuppressive Metabolite of Leflunomide, A77 1726", *Biochemical Pharm.*, vol. 52, pp. 527–534 (1996).

Ye, X. et al., "Analysis of EGFR Gene Transcription in Rat Embryo and Adult Tissues", *Shi Yan Sheng Wu Xue Bao*, vol. 24, No. 1, pp. 59–65 (Mar. 1991) (Abstract Only).

Yoshida, D. et al., "In Vitro Inhibition of Cell Proliferation, Viability, and Invasiveness in U87MG Human Glioblastoma Cells by Estramustine Phosphate", *Neurosurgery*, vol. 39, No. 2, pp. 360–366 (Aug. 1996).

Zheng, J. et al., "2.2 Å Refined Crystal Structure of the Catalytic Subunit of cAMP–Dependent Protein Kinase Complexed with MnATP and a Peptide Inhibitor", *Acta Cryst.*, vol. D49, Part 3, pp. 362–365 (May 1, 1993).

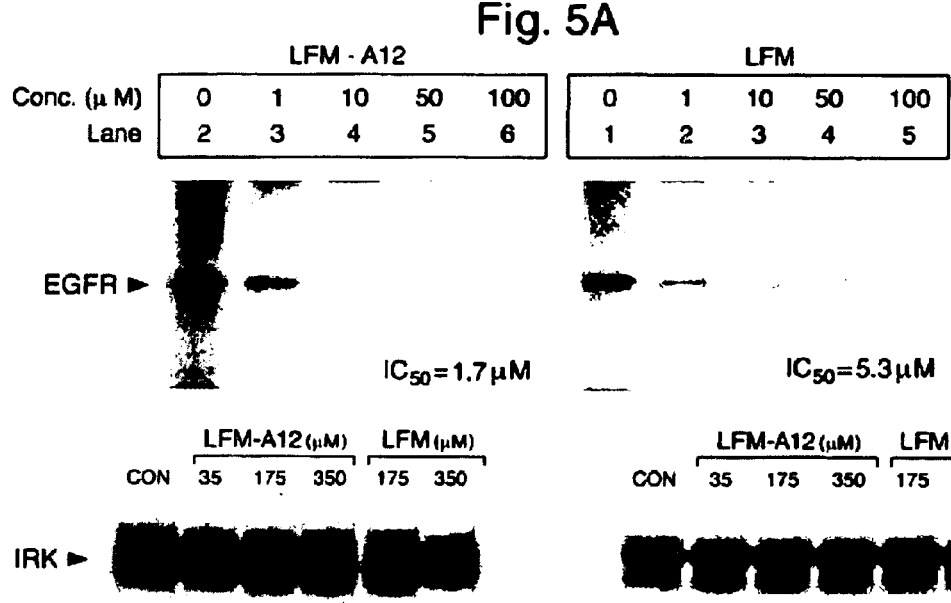

Fig. 5D
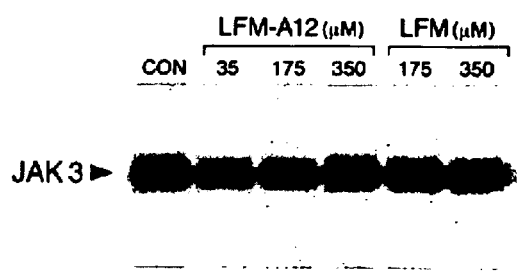
Fig. 5E
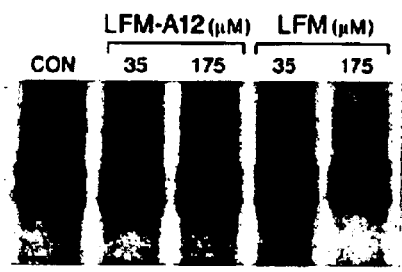
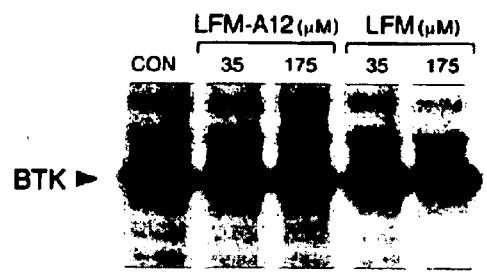
Fig. 5F

INHIBITORS OF THE EGF-RECEPTOR TYROSINE KINASE AND METHODS FOR THEIR USE

RELATED APPLICATIONS

This application is a continuation of U.S. patent application Ser. No. 09/273,002, filed Mar. 19, 1999 now U.S. Pat. No. 6,355,678, which itself claims priority under 35 U.S.C. §119(e) from U.S. Provisional Application 60/090,998, filed Jun. 29, 1998, and from U.S. Provisional Application 60/097,361, filed Aug. 21, 1998.

BACKGROUND OF THE INVENTION

Breast cancer is the most common form of malignancy in women, representing 32% of all new cancer cases and causing 18% of the cancer related deaths among women in the USA. Although the majority of patients with metastatic breast cancer will experience an initial response, survival is only modestly improved with contemporary chemotherapy programs. Consequently, the development of new anti-breast cancer drugs has become a high priority (Abrams, J. S., et al. M. *Cancer* 1994, 84, 1164).

Human epidermal growth factor (EGF) is a 53 amino acid, single-chain polypeptide (Mr 6216 daltons), which exerts biologic effects by binding to a specific cell membrane epidermal growth factor receptor (EGFR/ErbB-1). Many types of cancer cells display enhanced EGFR expression on their cell surface membranes (Khazaie, K., et al. R. B. *Cancer & Metasis Reviews* 1993, 12, 255). Enhanced expression of the EGFR on cancer cells has been associated with excessive proliferation and metastasis (Mendelsohn, J. and Baselga, J. *Biologic Therapy of Cancer: Principles & Practice* 1995, 607). Examples include breast cancer, prostate cancer, lung cancer, head and neck cancer, bladder cancer, melanoma, and brain tumors (Khazaie, K., et al. R. B. Cancer & Metasis Reviews 1993, 12, 255).

In breast cancer, expression of the EGFR is a significant and independent indicator for recurrence and poor relapse-free survival (Toi, M., et al. *European J. Cancer* 1991, 27, 977; Chrysogelos, S. A. and Dickson, R. B. *Breast Cancer Res. Treat.* 1994, 29, 29; Fox, S. B., et al. *Breast Cancer Res. Treat.* 1994, 29, 41). Additionally, it has been shown that the EGFR has an essential function for the survival of human breast cancer cells (Uckun, F. M., et al. *Clin. Can. Res.* 1998, 4, 901; Moyer, J. D., et al. *Cancer Res.* 1997, 57(21), 4838). Therefore, the development of PTK inhibitors which abrogate the enzymatic function of the EGFR tyrosine kinase has become a focal point in drug discovery research programs aimed at designing more effective treatment strategies for metastatic breast cancer (George-Nascimento, et al. *Biochemistry* 1988, 27, 797; Khazaie, K., et al. R. B. *Cancer & Metasis Reviews* 1993, 12, 255; Fry, D. W. and Bridges, A. J. *Curr. Opin. BiotechnoL* 1995, 6, 662; Wakeling, A. E., et al. *Breast Cancer Research & Treatment* 1996, 38, 67).

The primary metabolite of the anti-inflammatory leflunomide N-(4-trifluoromethylphenyl)-5-methylisoxazol-4-carboxamide, has been identified as an inhibitor of the EGFR kinase (Parnham, M. J. *Exp. Opin Invest. Drugs* 1995, 4, 777; Xu, X., et al. *Biochem. Pharmacol.* 1996, 52, 527; Xu, X., et al. *J. Biol. Chem.* 1995, 270, 12398; Bertolini, G., et al. *J. Med. Chem.* 1997, 40, 2011; Mattar, T., et al. A. F. E. B. S. *Lett.* 1993, 334, 161). Despite the identification of this inhibitor of the EGFR kinase, however, there is a continuing need for novel anti-cancer drugs. In particular, there is a need for anti-cancer drugs which are more potent or more selective than existing drugs. There is also a need for anti-cancer drugs that operate by novel mechanisms, and thus, may be useful against cancers that do not respond to, or have developed resistance to, existing therapies.

SUMMARY OF THE INVENTION

Applicants have discovered compounds that selectively inhibit EGFR tyrosine kinase, without affecting the activity of other PTKs. A representative compound of the invention was also found to inhibit the proliferation and in vitro invasiveness of EGFR positive human breast cancer cells at micromolar concentrations. Thus, the compounds of the invention are useful for treating cancer (e.g. breast cancer). The compounds are also useful as pharmacological tools that can be used to further investigate EGFR kinase function, or can be used in competitive binding assays to help identify other agents that may be useful as pharmaceuticals.

Accordingly, the invention provides a compound of the following formula I:

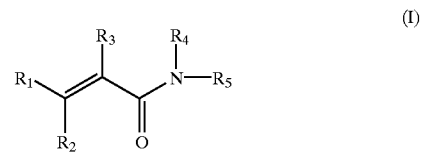

where:
$R_1$ is $(C_1-C_3)$alkyl, $(_3-C_6)$cycloalkyl, phenyl, or $NR_aR_b$;
$R_2$ is hydroxy, $(C_1-C_6)$alkoxy, or $(C_1-C_6)$alkanoyloxy;
$R_3$ is cyano, or $(C_1-C_3)$alkanoyl;
$R_4$ is hydrogen, or $(C_1-C_3)$alkyl;
$R_5$ is aryl, or heteroaryl;
$R_1$ and $R_b$ are each independently hydrogen, or $(C_1-C_3)$ alkyl; or $R_a$ and $R_b$ together with the nitrogen to which they are attached are pyrrolidino, piperidino, morpholino, or thiomorpholino;
wherein any aryl, or heteroaryl of $R_1$ and $R_5$ is optionally substituted with one or more (e.g., 1, 2, or 3) substituents independently selected from halo, nitro, cyano, hydroxy, trifluoromethyl, trifluoromethyl, trifluoromethoxy, $(C_1-C_3)$alkoxy, $(C_1-C_3)$alkyl, $(C_1-C_3)$alkanoyl, —$S(O)_2R_c$, or $NR_aR_b$; wherein $R_c$ is $(C_1-C_3)$alkyl, or aryl or a pharmaceutically acceptable salt thereof.

Prefereably, if $R_5$ is phenyl, the phenyl is substituted by —$S(O)_2R_c$, or is substituted by halo and at least one other substituent.

Preferred compounds of formula I include those of formula II:

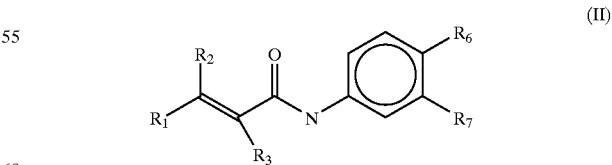

where $R_1$ is $(C_1-C_6)$alkyl, optionally substituted by 1, 2, or 3 substituents selected from the group consisting of halo, hydroxy, amino, $(C_1-C_6)$alkoxy, and $(C_1-C_6)$alkanoyloxy; $R_2$ is hydroxy, $(C_1-C_6)$alkoxy, $(C_1-C_6)$alkanoyloxy; $R_3$ is cyano, alkanoyl; $R_6$ is amino, hydroxy, cyano, nitro, $(C_1-C_6)$ alkyl, halo$(C_1-C_6)$alkyl, $(C_1-C_6)$alkoxy, halo$(C_1-C_6)$ alkoxy, (C$_1$–C$_6$)alkanoyl, or (C$_1$–C$_6$)alkanoyloxy; and R$_7$ is H, NH$_2$, CH$_3$, OH, CF$_3$, or halo, preferably, halo is Br or Cl; or a pharmaceutically acceptable salt thereof.

Particularly compounds of formula I include those of formulae III–VI:

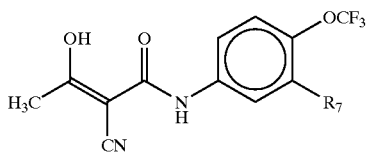
(III)

where R$_7$ is H, NH$_2$, CH$_3$, OH, CF$_3$, or halo. Preferably, halo is Br or Cl.

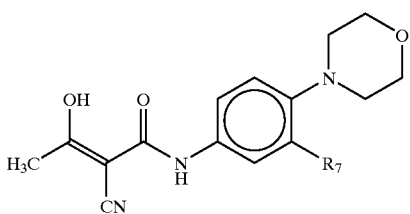
(IV)

where R$_7$ is H, NH$_2$, CH$_3$, OH, CF$_3$, or halo. Preferably, halo is F or Cl.

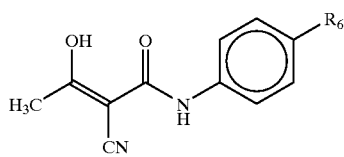
(V)

where R$_6$ is NH—CH$_3$ or OCH$_3$.

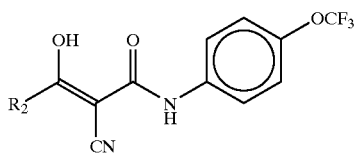
(VI)

where R$_2$ is —CH$_2$—CH$_2$X and X is halo, preferably F; or R$_2$ is —CH$_2$CF$_3$; or R$_2$ is:

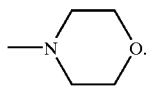

The invention also provides a pharmaceutical composition comprising a compound of formula I; or a pharmaceutically acceptable salt thereof, and a pharmaceutically acceptable carrier.

A particularly useful compound of the invention is LFM 12, having the structural formula:

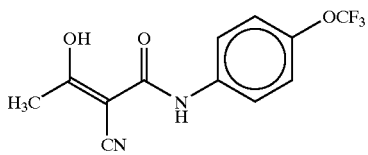

The invention also provides a therapeutic method for treating diseases in which EGFR is overexpressed, particularly cancers (e.g. breast cancer) comprising administering to a mammal in need of such therapy, a compound of the invention, e.g., of formulae I–VI; or a pharmaceutically acceptable salt thereof.

The invention also provides a compound for use in medical therapy preferably for use in treating cancer), as well as the use of a compound of formulae I–VI for the manufacture of a medicament for the treatment of a pathological condition or symptom in a mammal, such as a human, which is associated cancer (e.g. breast cancer).

The invention also provides a homology model representing the structure of the EGF-R kinase domain and a docking procedure, which are useful to rationally design compounds predicted to bind favorably to EGF-R and inhibit EGFR-TK activity. Using this model, leflunomide metabolite analogs were designed and found to have potent inhibitory activity against EGFR TK (IC$_{50}$ value of 1.7 µM in EGF-R inhibition assays, killing >99% of human breast cancer cells in vitro by triggering apoptosis). New potent LFM analogs as active inhibitors of the EGF-R tyrosine kinase are designed and confirmed using this model.

The invention also provides processes and novel intermediates, described herein, that are useful for preparing compounds of formulae I, II, IV–VI.

BRIEF DESCRIPTION OF THE FIGURES

FIG. 1A is a molecular surface model showing the plan as active site. FIG. 1B is a stereoview of the catalytic site of the EGF-R kinase domain with the inhibitor binding region represented as a triangular-shaped grid.

FIG. 2A is a ribbon (Cα chain) representation of the homology model of the EGFR kinase domain and a space filling model of the compound LFM-A12 which was docked into the catalytic site. The N-lobe shown in blue is primarily composed of β-sheets and the C-lobe shown in gray is mostly helical. The hinge region is shown in peach. Prepared using Molscript and Raster3D programs (Bacon, D. J. and Anderson, W. F. J. Molec. Graphics 1988, 6, 219; Kraulis, P. J. Appl. Cryst. 1991, 24, 946; Merritt, E. A. and Murphy, M. E. P. Acta Cryst. 1994, D50, 869).

FIG. 2B is a space filling representation of the catalytic site residues of the EGFR kinase domain. The Cα chain of EGFR is represented as a pink ribbon and the residues comprising the hinge region are shown in blue. One corner of the triangular binding region is located between the T766 (peach) and D831 (lavender) residues. The second corner bordering the binding region is located at R817 shown in green and the third corner is near the lower left side of the hinge region. A ball and stick model of the inhibitor LFM-A12 is shown in multicolor and represents a favorable orientation of this molecule in the kinase active site of EGFR. Prepared using InsightII program (InsightII, Molecular Simulations Inc. 1996, San Diego, Calif.).

FIGS. 5A–5F are anti-phosphotyrosine Western blots showing selective inhibition of EGFR tyrosine kinase by LFM-A12. FIG. 5A shows EGFR immune complexes from lysates of MDA-MB-231 human breast cancer cells treated with LFM or LFM-A12 for 1 hour and then assayed for tyrosine kinase activity, as described in Example 5. FIG. 5B shows a lack of inhibition of IRK immunoprecipitated from HepG2 hepatoma cells in immune complex kinase assays after treatment with LFM or LFM-A12. FIG. 5C shows a lack of inhibition of HCK immunoprecipitated from transfected COS7 cells in immune complex kinase assays after treatment with LFM or LFM-A12. FIGS. 5D–5F show a lack of inhibition of JAK3, JAK1, and BTK immunoprecipitated from lysates of transfected insect ovary cells.

FIG. 6A shows the superimposed backbones of the catalytic site residues of the kinase domain homology models of EGFR (white), PTK (peach) and crystal structure coordinates of HCK (blue), with selected residues at positions A, B, and C. LFM-A12 is shown in multicolor and represents its docked positionin BTK, which is also similar to its docked position in HCK. The white dotted surface area represents the Connolly surface of LFM-A12. FIG. 6B shows superimposed backbones of the catalytic site residues of the kinase domain homology models of EFGR (white), JAK3 (pink) and crystal structure coordinates of IRK (green), with selected residues at positions A, B, and C. LFM-A12 is shown in multicolor and represents its docked positionin EGFR which is also similar to its docked position in IRK and JAK3. The white dotted surface area represents the Connolly surface of LFM-A12.

FIG. 7A is a bar graph showing the invasion of LFM-A12-treated breast cancer cells through the Matrigel matrix was inhibited in a dose-dependent fashion. The invasion of LFM-treated breast cancer cells was inhibited to a lesser extent. The mean $IC_{50}$ values were 28.4 $\mu$M for LFM-A12 and 97.0 $\mu$M for LFM. FIG. 7B is a series of photographs showing microscopic evidence for the dose-dependent reduction of the numbers of migrated MDA-MB-231 cells after treatment with LFM-A12.

DETAILED DESCRIPTION OF THE INVENTION

Figure 1A:
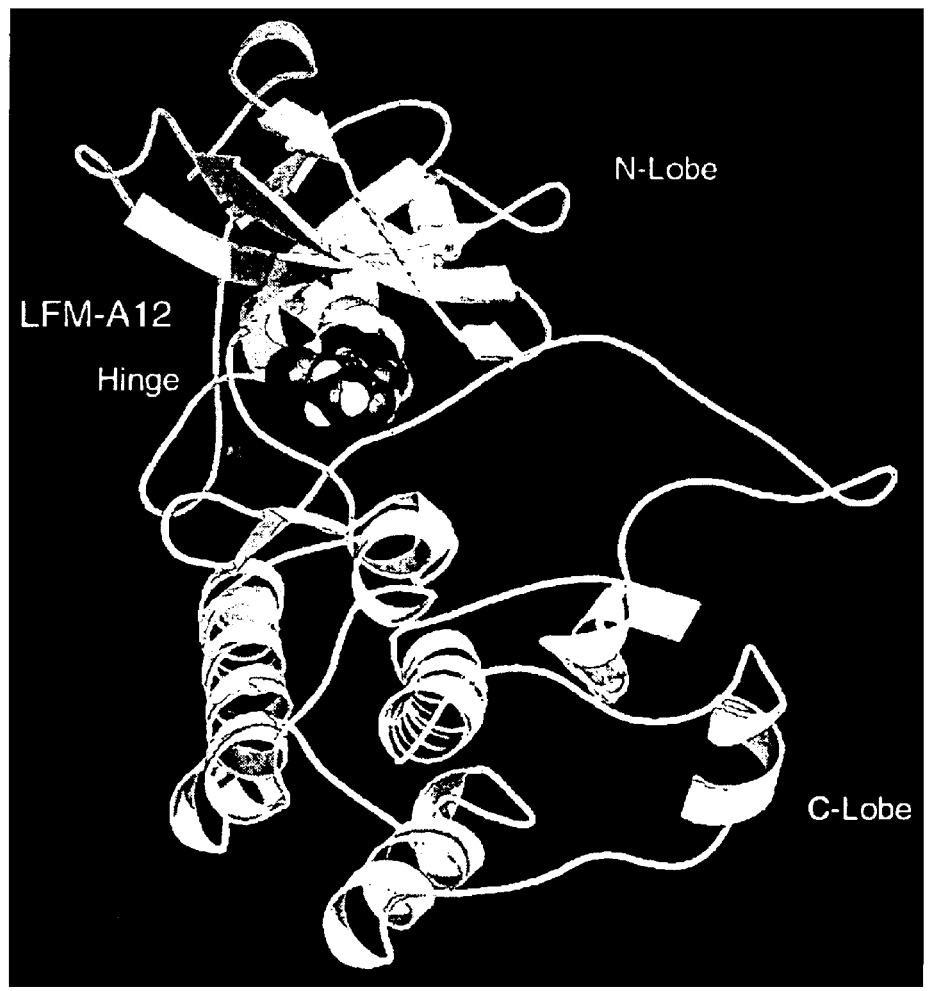
FIGS. 1A and 1B show a homology model for the EGF-R kinase domain.

The following definitions are used, unless otherwise described: halo is fluoro, chloro, bromo, or iodo. Alkyl, alkoxy, etc. denote both straight and branched groups; but reference to an individual group such as "propyl" embraces only the straight chain group, a branched chain isomer such as "isopropyl" being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine a compounds ability to inhibit EGFR tyrosine kinase using the standard tests described herein, or using other similar tests which are well known in the art.

Specific and preferred values listed below for substituents and ranges, are for illustration only; they do not exclude other defined values or other values within defined ranges for the substituents.

The term "prodrug moiety" is a substitution group which facilitates use of a compound of the invention, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolized in vivo.

Compounds of the Invention

Specific inhibitors of EGFR tyrosine kinase include those of formula I:

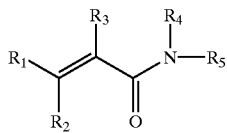
(I)

where:
- $R_1$ is $(C_1-C_3)$alkyl, $(_3-C_6)$cycloalkyl, phenyl, or $NR_aR_b$;
- $R_2$ is hydroxy, $(C_1-C_3)$alkoxy, or $(C_1-C_6)$alkanoyloxy;
- $R_3$ is cyano, or $(C_1-C_3)$alkanoyl;
- $R_4$ is hydrogen, or $(C_1-C_3)$alkyl;
- $R_5$ is aryl, or heteroaryl;
- $R_a$ and $R_b$ are each independently hydrogen, or $(C_1-C_3)$ alkyl; or $R_a$ and $R_b$ together with the nitrogen to which they are attached are pyrrolidino, piperidino, morpholino, or thiomorpholino;
- wherein any aryl, or heteroaryl of $R_1$ and $R_5$ is optionally substituted with one or more (e.g., 1, 2, or 3) substituents independently selected from halo, nitro, cyano, hydroxy, trifluoromethyl, trifluoromethyl, trifluoromethoxy, $(C_1-C_3)$alkoxy, $(C_1-C_3)$alkyl, $(C_1-C_3)$alkanoyl, $-S(O)_2R_c$, or $NR_aR_b$; wherein $R_c$ is $(C_1-C_3)$alkyl, or aryl or a pharmaceutically acceptable salt thereof;

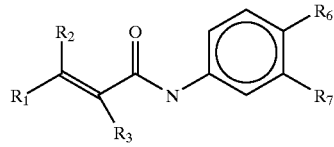
(II)

Preferred are compounds of formula II, where $R_1$ is $(C_1-C_6)$alkyl, optionally substituted by 1, 2, or 3 substituents selected from the group consisting of halo, ΔΔΔΔ, $(C_1-C_6)$alkoxy, $R_2$ is hydroxy, $(C_1-C_6)$alkoxy, $(C_1-C_6)$ alkanoyloxy; $R_3$ is cyano, alkanoyl; $R_4$ is amino, hydroxy, cyano, nitro, $(C_1-C_6)$alkyl, halo$(C_1-C_6)$alkyl, $(C_1-C_6)$ alkoxy, halo$(C_1-C_6)$ alkoxy, $(C_1-C_6)$alkanoyl, or $(C_1-C_6)$ alkanoyloxy; and $R_5$ is H, $NH_2$, $CH_3$, OH, $CF_3$, or halo, preferably halo is Br or Cl; or a pharmaceutically acceptable salt thereof.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; and $(C_2-C_6)$alkanoyloxy can be acetoxy, propanoyloxy, butanoyloxy, isobutanoyloxy, pentanoyloxy, or hexanoyloxy. A specific value for $R_1$ is $(C_1-C_6)$alkyl, optionally substituted by halo, hydroxy, amino, or $(C_1-C_6)$ alkoxy.

Another specific value for $R_1$ is $(C_1-C_6)$alkyl.

A preferred value for $R_1$ is methyl.

A preferred value for $R_1$ is hydroxy.

A preferred value for $R_3$ is cyano.

A preferred value for $R_4$ is trifluoromethoxy.

A preferred compound is a compound of formula I wherein $R_1$ is $(C_1-C_6)$alkyl; $R_2$ is hydroxy, $(C_1-C_6)$alkoxy, or $(C_1-C_6)$alkanoyloxy; $R_3$ is cyano; and $R_4$ trifluoromethoxy; or a pharmaceutically acceptable salt thereof.

Another preferred compound is a compound of formula I wherein $R_1$ is methyl; $R_2$ is hydroxy; $R_3$ is cyano; and $R_4$ trifluoromethoxy; or a pharmaceutically acceptable salt thereof.

Preferred compounds of the invention include novel analogs of LFM designed to better fit the EGFR binding pocket and better interact with amino acid residues forming contacts within the pocket. These compounds of the invention fall within four groups, or types, and are more fully described below in Example 6. These compounds have the following structural formulae (III–VI):

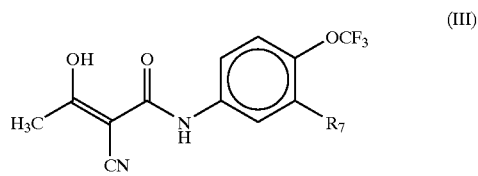
(III)

where $R_5$ is H, $NH_2$, $CH_3$, OH, $CF_3$, or halo. Preferably, halo is Br or Cl.

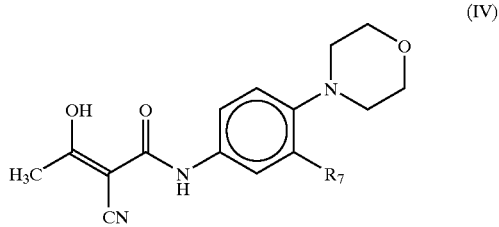
(IV)

where $R_5$ is H, $NH_2$, $CH_3$, OH, $CF_3$, or halo. Preferably, halo is F or Cl.

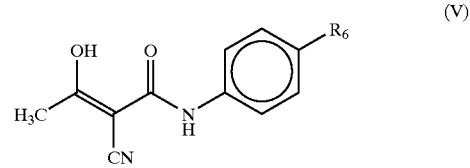
(V)

where $R_4$ is $NH-CH_3$ or $OCH_3$.

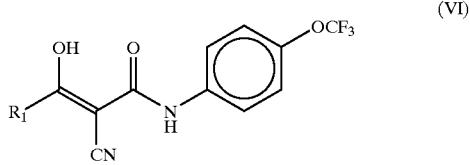
(VI)

where $R_1$ is $-CH_2-CH_2X$ and X is halo, preferably F; or $R_1$ is $-CH_2CF_3$; or $R_1$ is: 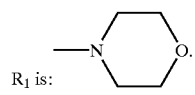

Processes for preparing compounds of formulae I–VI are provided as further embodiments of the invention and are illustrated by the following procedures and Examples in which the meanings of the generic radicals are as given above unless otherwise qualified. A compound of formula I wherein $R_2$ is hydroxy, can conveniently be prepared by treating an intermediate of formula A: with an acid chloride of formula: $R_1COCl$.

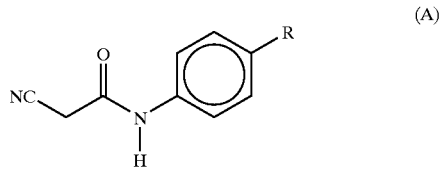

(A)

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention may have attached thereto functional groups to provide a prodrug derivative. The prodrug deriviative facilitates use of the drug in the body, for example, by facilitating entry into cells. The prodrug derivative may be cleaved or not in the active compound.

Pharmaceutical Compositions

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

Conjugation to a Targeting Moiety

The compounds of the invention may be conjugated to a targeting moiety for targeted delivery to a desired cell. Useful targeting moieties are antibodies or specific ligands that bind to an antigen or ligand receptor on the specific target cells. For example, the EGFR TK inhibitors of the invention may be targeted to EGFR-expressing cells by conjugation of the inhibitor to an anti-EGFR antibody, or by conjugation to EGF. Other useful targeting moieties include molecules which bind or associate with the EGFR, including TGF-alpha, Erb2, Erb3, Erb4, or antibodies against these molecules.

To form the conjugates of the invention, a targeting moiety, which is often a polypeptide molecule, is bound to the compounds of the invention at reactive sites, including $NH_2$, SH, CHO, COOH, and the like. Specific linking agents are used to link the compounds. Preferred linking agents are chosen according to the reactive site to which the targeting moiety is to be attached.

Methods for selecting an appropriate linking agent and reactive site for attachment of the targeting moiety to the compound of the invention are known, and are described, for example, in Hermanson, et.al., *Bioconjugate Techniques*, Academic Press, 1996; Hermanson, et.al., *Immobilized Affinity Ligand Techniques*, Academic Press, 1992; and *Pierce Catalog and Handbook,* 1996, ppT155–T201.

Pharmaceutical Additives

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions. For topical administration, the present compounds may be applied in pure form, i.e., when they are liquids. However, it will generally be desireable to administer them to the skin as compositions or formulations, in combination with a detematology acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Treatment Methods

The EGFR-tyrosine kinase inhibitors of the invention are useful to inhibit the activity of EGFR-tyrosine kinasae. In particular, the compounds are usful in the treatment of diseases and pathological conditions that involve cells expressing EGFR. Most importantly, the inhibitors of the present invention provide a treatment for selectively inhibiting EGFR tyrosine kinase, without significant inhibition of other tyrosine kinases, such as the Src family, Tec family, and Janus family tyrosine kinases.

Many known pathologic conditions involve the EGFR and the activity of the EGFR tyrosine kinase. These include cancers such as breast cancer, prostate cancer, lung cancer, brain tumor, bladder cancer, and colon cancer. The EGFR TK inhibitors of the invention are delivered to the EGFR, and particularly to the kinase binding domain of the receptor, in order to inhibit the kinase activity. The compounds of the invention may be administered to cancer patients to treat exsisting cancer, or be administered to those at risk for developing cancer, including genetic, occupational, and nutritional predisposition to cancer.

Additional disorders known to involve EGFR and its TK include atherosclerosis, disorders of vascular smooth muscle cells, and endothelial cells involved in tumor angiogenesis.

Dosage

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient.

Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention may be better understood with reference to the following Examples, which are not intended to limit the scope of the invention.

EXAMPLE 1

Crystal Structures of Leflunomide Metabolite and Its Analogs

Small molecule X-ray crystal structures were obtained for 10 of the 15 leflunomide metabolite analogs studied herein. The compounds were crystallized using various solvents by evaporation, vapor diffusion or liquid—liquid diffusion. X-ray data on single crystals were collected on a SMART CCD detector (Bruker Analytical X-ray Systems, Madison, Wis.) using MoKα radiation (λ=0.7107 Å). The space group for each crystal was determined based on systematic absences and intensity statistics. A direct methods solution provided most of the non-hydrogen atoms from the electron density map. Several full-matrix least squares/difference Fourier cycles were performed to locate the remaining non-hydrogen atoms. All non-hydrogen atoms were refined with anisotropic thermal parameters. Hydrogen atoms were placed in ideal positions and refined as riding atoms with relative isotropic temperature factors. The structure was refined using full-matrix least-squares data on $F^2$.

Crystal structure calculations were performed using a Silicon Graphics INDY R4400-SC computer (Silicon Graphics Inc., Mountain View, Calif.) or Pentium computer using the SHELXTL V 5.0 (Sheldrick, G. SHELXTL Bruker Analytical X-ray Systems, Madison, Wis.) suite of programs. The crystal data, experimental parameters, and refinement statistics are summarized in Table 1.

TABLE 1

Crystal data, data collection and refinement statistics for leflunomide metabolite analogs.

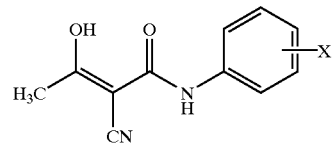

| Compound | LFM | LFM-A1 | LFM-A2 | LFM-A7 | LFM-A8 |
|---|---|---|---|---|---|
| X | p-CF$_3$ | p-Br | p-Cl | o-F | m-CF$_3$ |
| Empirical formula | C$_{12}$H$_9$F$_3$N$_2$O$_2$ | C$_{11}$H$_9$BrN$_2$O$_2$ | C$_{11}$H$_9$ClN$_2$O$_2$ | C$_{11}$H$_9$FN$_2$O$_2$ | C$_{12}$H$_9$F$_3$N$_2$O |
| Crystal system | Triclinic | Triclinic | Monoclinic | Monoclinic | Triclinic |
| Space group | P-1 | P-1 | P2$_1$/n | P2$_1$/c | P-1 |
| Cell constants | a = 9.4862(6)Å | A = 4.9906(2)Å | a = 13.4297(10)Å | a = 8.9641(8)Å | a = 5.2176(6)Å |
| | b = 11.5511(7)Å | B = 9.3735(3)Å | b = 3.8073(3)Å | b = 14.1215(12)Å | b = 10.4929(2)Å |
| | c = 12.0013(7)Å | c = 11.8869(1)Å | c = 21.201(2)Å | c = 8.3270(7)Å | c = 12.0757(14)Å |
| | α = 96.126(2)° | α = 77.394(2)° | β = 98.779(2)° | β = 101.023(2)° | α = 67.719(2)° |
| | β = 105.914(1)° | β = 86.4042)° | | | β = 78.921(2)° |
| | γ = 110.571(2)° | γ = 88.065(2)° | | | γ = 78.915(2)° |
| Z | 4 | 2 | 4 | 4 | 2 |
| Formula weight | 270.21 | 281.11 | 236.66 | 220.20 | 270.21 |
| Reflections collected | 5372 | 2741 | 5021 | 5017 | 3660 |
| Independent reflections | 3715 | 1836 | 1849 | 1788 | 1967 |
| R indices (I > 2σ(I)) | R1 = 0.090 wR2 = 0.214 | R1 = 0.062 wR2 = 0.152 | R1 = 0.086 wR2 = 0.205 | R1 = 0.047 wR2 = 0.115 | R1 = 0.060 wR2 = 0.139 |

| Compound | LFM-A9 | LFM-A10 | LFM-A11 | LFM-A12 | LFM-A13 |
|---|---|---|---|---|---|
| X | m-Br | m-Cl | m-F | p-OCF$_3$ | 2,5-diBr |
| Empirical formula | C$_{11}$H$_9$BrN$_2$O$_2$ | C$_{11}$H$_9$ClN$_2$O$_2$ | C$_{11}$H$_9$FN$_2$O$_2$ | C$_{12}$H$_9$F$_3$N$_2$O$_3$ | C$_{11}$H$_8$Br$_2$N$_2$O$_2$ |
| Crystal system | Triclinic | Triclinic | Monoclinic | Triclinic | Monoclinic |
| Space group | P-1 | P-1 | P2$_1$/c | P-1 | P2$_1$/c |
| Cell constants | a = 5.2782(2)Å | A = 5.2955(4)Å | a = 4.7724(1)Å | a = 4.6460(1)Å | a = 5.6134(1)Å |
| | b = 10.2335(4)Å | B = 10.0638(7)Å | b = 24.1536(1)Å | b = 9.0781(3)Å | b = 9.9847(3)Å |
| | c = 11.5754(4)Å | c = 11.2503(8)Å | c = 9.1565(2)Å | c = 14.6881(1)Å | c = 21.5896(2)Å |
| | α = 69.792(1)° | α = 103.951(2)° | β = 95.937(1)° | α = 94.488(2)° | β = 93.639(1)° |
| | β = 78.592(1)° | β = 102.516(1)° | | β = 91.658(2)° | |
| | γ = 75.837(1)° | γ = 105.121(2)° | | γ = 93.682(2)° | |
| Z | 2 | 2 | 4 | 2 | 4 |
| Formula weight | 281.11 | 236.66 | 220.20 | 286.21 | 360.00 |
| Reflections collected | 3713 | 3410 | 6832 | 3856 | 5918 |
| Independent reflections | 1926 | 1829 | 1851 | 2059 | 2109 |
| R indices (I > 2σ(I)) | R1 = 0.056 wR2 = 0.145 | R1 = 0.051 WR2 = 0.1277 | R1 = 0.051 wR2 = 0.149 | R1 = 0.0741 wR2 = 0.18 | R1 = 0.040 wR2 = 0.094 |

EXAMPLE 2

Construction of a Homology Model for the EGF Receptor Kinase Domain

A homology model for the EGFR kinase domain was constructed based on a structural alignment of the sequence of EGFR (accession # P00533, SWISS-PROT, Univ. of Geneva, Geneva, Switzerland) obtained from Genbank (National Center for Biotechnology Information, Bethesda, Md.) with the sequences of known crystal structures of other protein kinases (kinase domains of HCK (Sicheri, F., et al. *Nature* 1997, 385, 602), FGFR (Mohammadi, M., et al. *Science* 1997, 276, 955), IRK (Hubbard, S. R. *The E. M. B. O. Journal* 1997, 16, 5572), and cAPK (Zheng, J., et al. *Acta Cryst.* 1993, D49, 362)).

A multiple sequence alignment of HCK, FGFR, IRK, and cAPK with that of EGFR was carried out manually, conserving the overall secondary structure within the family. Once the correspondence between amino acids in the reference and model sequences were made, the coordinates for the structurally conserved regions were assigned based on the coordinates of the reference proteins. Insertions, deletions and mutations were incorporated into the template structure to build an initial model. The final model of EGFR was subjected to energy minimization to refine the molecular structure so that any steric strain introduced during the model-building process could be relieved (Brunger, A. T. X-PLOR 1992, New Haven, Conn.).

The model was screened for unfavorable steric contacts and, if necessary, such side chains were remodeled either by using a rotamer library database or by manually rotating the respective side chains. The modeling was carried out on a Silicon Graphics INDIGO2 computer (Silicon Graphics Inc., Mountain View, Calif.) using the Homology module in INSIGHTII (InsightII, Molecular Simulations Inc. 1996, San Diego, Calif.). The final homology model of the EGFR kinase domain had an rms deviation of 0.006 Å from ideal bond lengths and 2.0° from ideal bond angles after energy minimization. The above procedure was used to construct the homology model, and the homology model was used, in conjunction with small molecule crystal structures of the leflunomide analogs, for modeling studies of the EGF-R/LFM complexes.

Figure 1B:
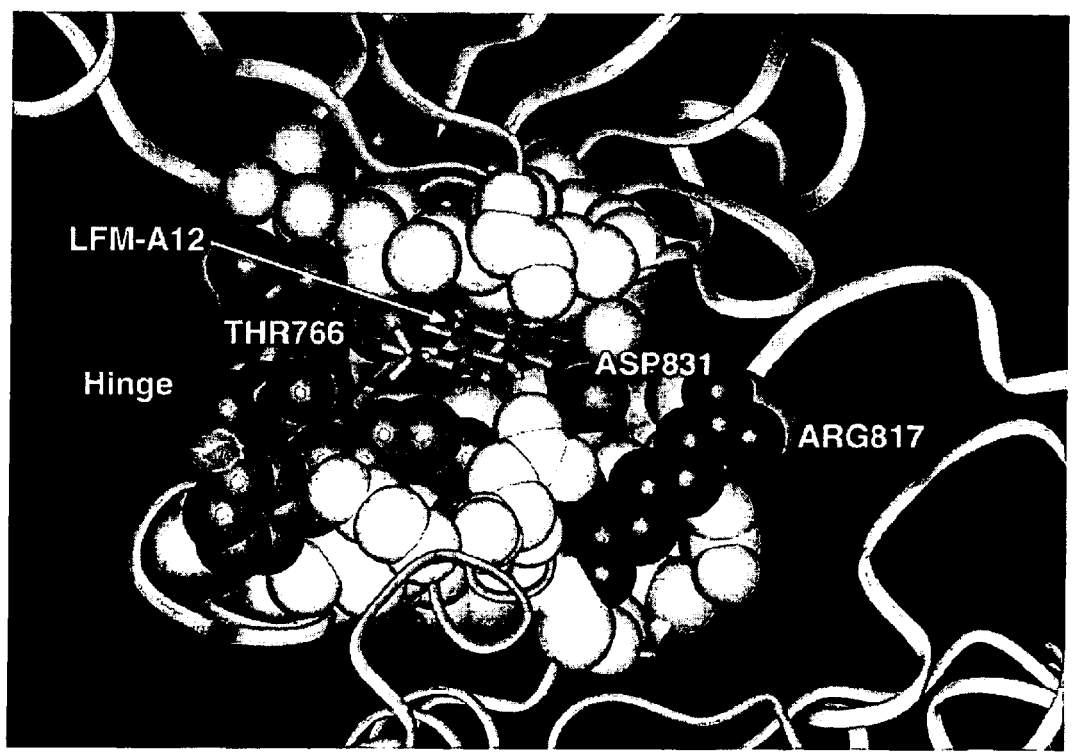
Figure 2A:
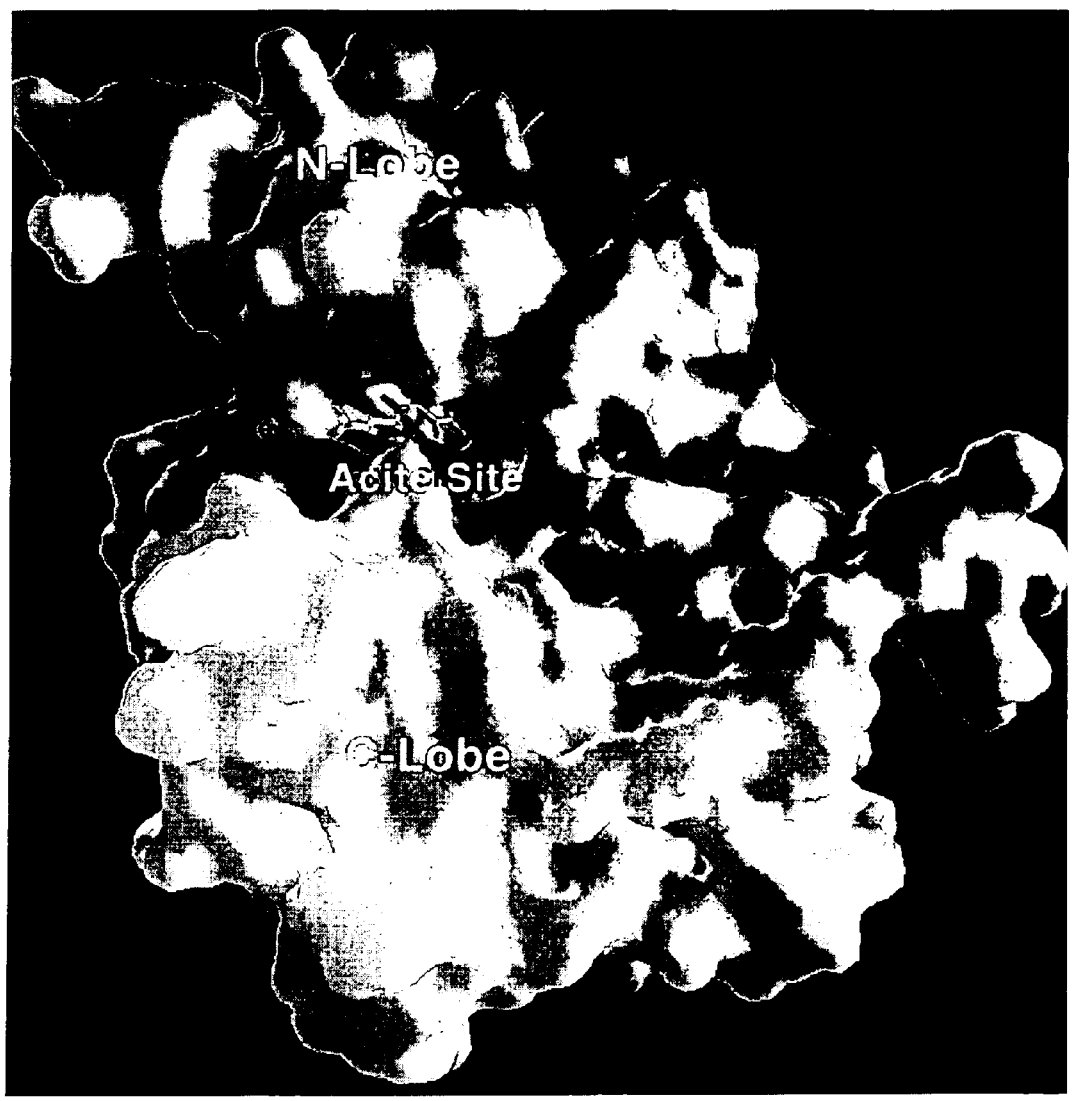
FIGS. 2A–2B are photographs showing the homology model of the EGFR kinase domain.
Figure 2B:
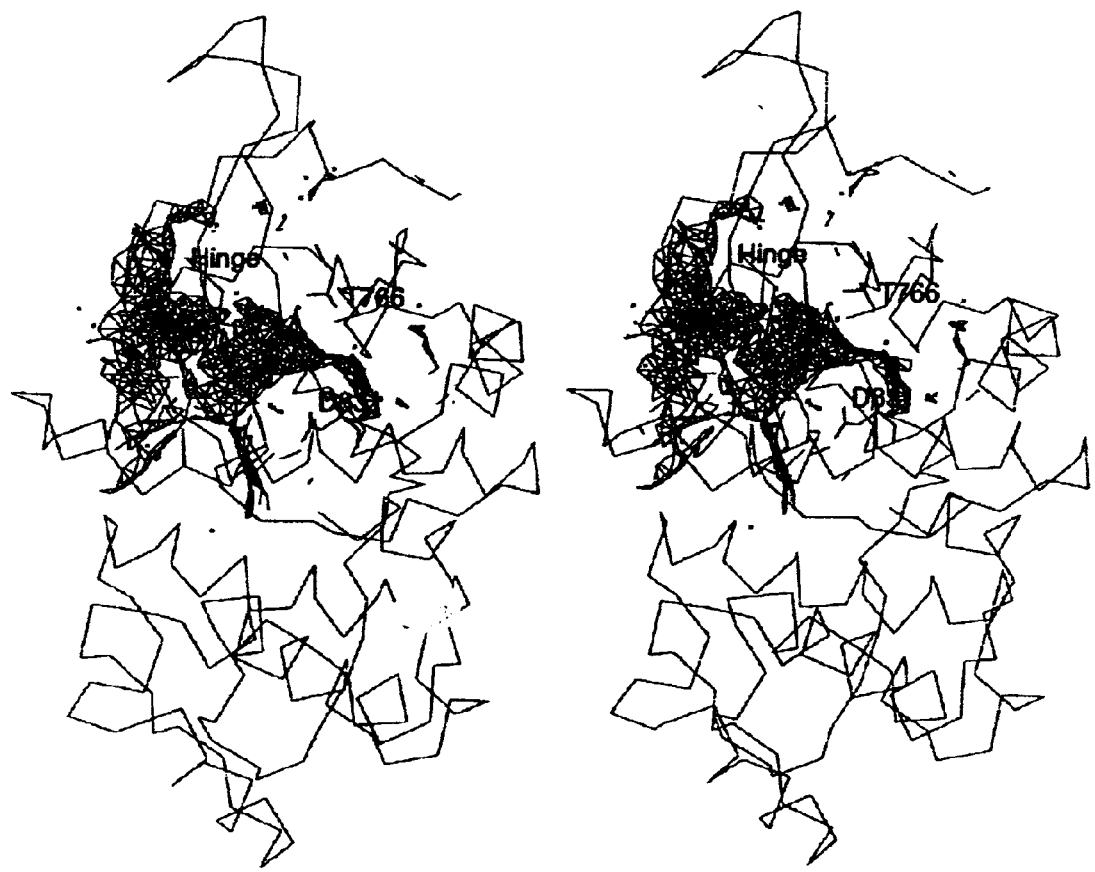

The modeled EGFR kinase domain has the expected protein kinase fold with the catalytic site in the center dividing the kinase domain into two lobes. It is composed of a smaller N-terminal lobe connected by a flexible hinge (residues 764 to 773) to a larger C-terminal lobe (See FIGS. 1A–1B and 2A–2C). The N-terminal lobe is rich in β-strands, while the C-terminal lobe is mostly helical. The catalytic site is defined by two β-sheets that form an interface at the cleft between the two lobes. The catalytic site of the EGFR kinase domain displays a remarkably planar triangular binding pocket, which can bind the base ring portion of ATP. The sides of this triangle are approximately 15 Å×12 Å×12 Å and the thickness of the binding pocket is approximately 7 Å, with an estimated volume of approximately 600 Å$^3$. The characteristics of this triangular region, which binds the base ring portion of ATP, was elucidated using a binding sphere surface calculated by the program SPHGEN in DOCK3.5. (Kuntz, I. D. et al., *J. Mol. Biol.,* 1982:161: 269–288). Two sides of the triangle can be visualized as beginning at an apex located between Thr$^{766}$ (peach residue in FIG. 1B) and Asp$^{831}$ (lavender residue in FIG. 1B), and extending towards the solvent-accessible opening of the catalytic site. One side of the triangle extends from the apex along the hinge region of the catalytic site (blue residues in FIG. 1B), and a second side extends from the apex to Arg$^{817}$ (green residue in FIG. 1B) which is immediately adjacent to the binding subsites for the sugar and triphosphate groups of ATP. The hinge region of the binding site is composed of residues 764 to 773 (FIG. 2). The third side of the triangle extends along the slot-shaped opening to the catalytic site.

The crystal structures of the HCK/quercetin complex (Sicheri, F., et al. *Nature* 1997, 385, 602) and two FGFR/inhibitor complexes (Mohammadi, M., et al. *Science* 1997, 276, 955) revealed that the reported three inhibitors of HCK and FGFR bind to the catalytic sites of the respective tyrosine kinases. When the catalytic sites are superimposed with EGFR, all atoms of the three PTK inhibitors fall within the plane of the triangle described previously, and each molecule is in close contact with the superimposed hinge region and Asp$^{831}$ of EGFR. Moreover, they characteristically occupy only half of the triangle, near the hinge region. This molecular fitting feature seems to correlate with tighter binding and may be an important determinant for effective inhibitor binding. Similarly, the size and planar shape of the catalytic site within the constructed EGFR kinase domain are likely to contribute to its ability to form energetically favorable interactions with planar molecules such as the LFM analogs described herein. These considerations are in agreement with conclusions derived from the structure-activity relationship analyses of pyrolo- and pyrazolo-quinazoline compounds (Palmer, B. D. et al. *J. Med. Chem.* 1997, 40, 1519) and were therefore incorporated into the modeling strategy.

While most of the catalytic site residues of the EGFR kinase domain were conserved relative to other PTKs, we noted a few specific variations. EGFR residues Leu$^{694}$, Val$^{702}$, Lys$^{721}$, and Ala$^{719}$ are conserved in EGFR, HCK, FGFR and IRK. Residues Asn$^{818}$ and Asp$^{831}$ (opposite to the hinge) are conserved in EGFR, HCK, FGFR, IRK, BTK, JAK1, and JAK3. Residues Cys$^{751}$ and Thr$^{830}$ are specific for EGFR but vary in BTK (Val, Ser), JAK1 (Val, Gly), JAK3 (Val, Ala), IRK (Val, Gly), and HCK (Val, Ala). Residues Thr$^{766}$ and Leu$^{768}$ in the hinge region changes to Met and Leu in IRK, Met and Phe in JAK1, Met and Tyr in JAK3, and to Thr and Tyr in BTK. The right side of the binding pocket (FIGS. 2–4) contains Cys$^{773}$ in EGFR and is therefore considerably more hydrophobic than the corresponding residue of PDGFR (Asp), FGFR (Asn), JAK1 (Ser), HCK (Ser), and IRK (Asp). These residue differences provide a basis for designing selective inhibitors of the EGFR kinase domain.

Thus, the catalytic site of the EGFR kinase has a triangular shaped binding region which contains some specific nonconserved residues. This information, combined with the homology model developed and described above, can be used to design compounds that will possess activity as EGFR kinase inhibitors.

Figure 3:
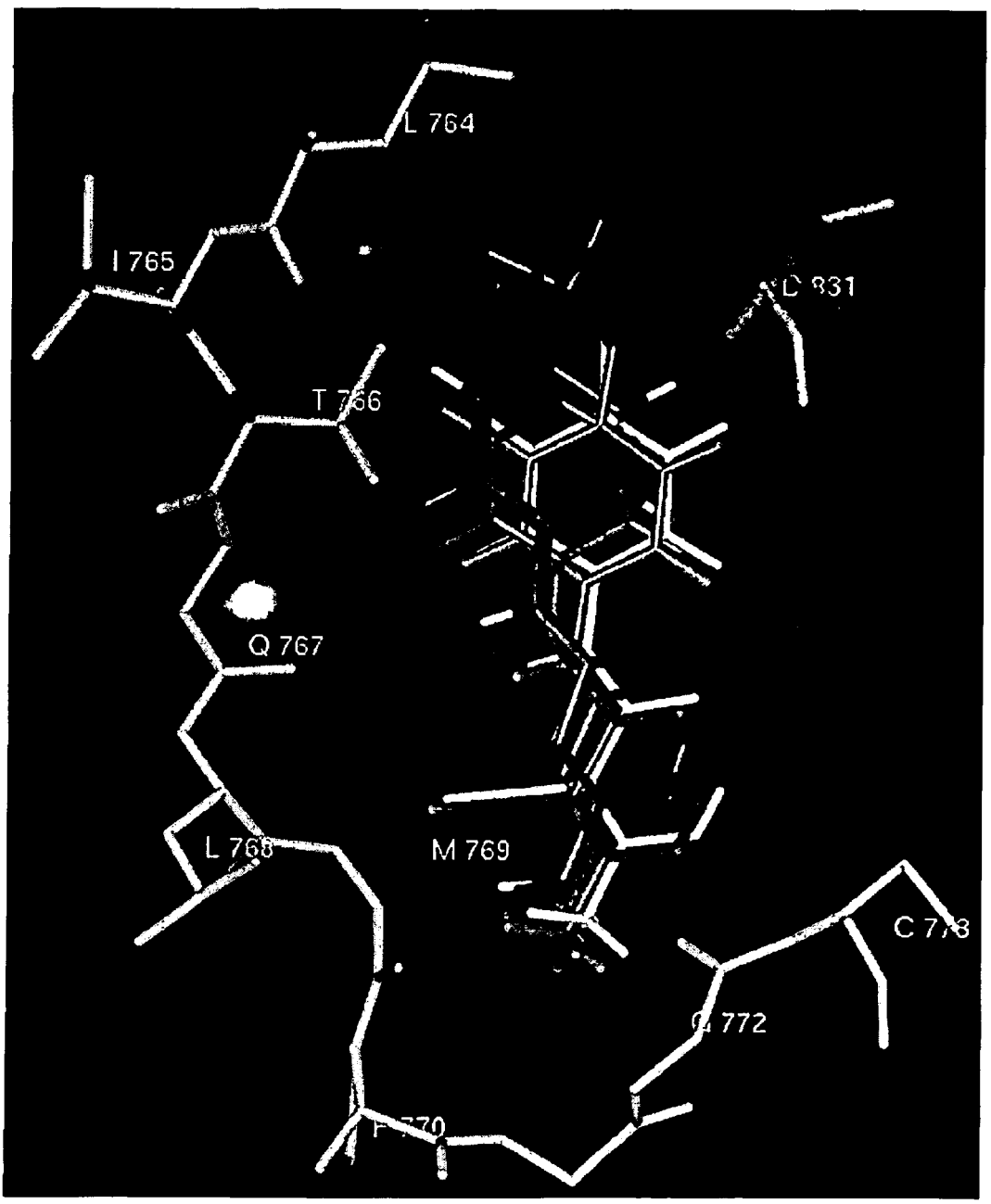
FIG. 3 shows the superimposed docked positions of the para substituted LFM analogs at the active site of the EGFR tyrosine kinase. The residues in the active site are shown in pink. LFM: para-$CF_3$ substituted compound (active metabolite of leflunomide, green); LFM-A1: para-Br substituted analog (blue); LFM-A2: para-Cl substituted analog (red); LFM-A3: para-F substituted LFM analog (white). LFM-A12: para-$OCF_3$ substituted LFM analog (gold).

Selectivity for a particular tyrosine kinase can also be achieved by extending the binding area to the other half of the triangle (opposite the hinge), as has been observed in one of the FGF-R inhibitor structures (Mohammadi, M., et al. *Cell* 1996: 86, 577–87) and (Connolly, M. L., *Science,* 1983, 221: 709–13). The difference in binding affinity is provided by Phe489 which extends from a beta hairpin toward the inhibitor. EGF-R has a shorter and more rigid beta hairpin that FGFR which would present some limitations to this strategy. The non-conserved residue Arg 817 could also provide some binding discrimination if the inhibitor binds nearby. We concluded from our modeling studies that the catalytic site of the EGF-R has specific features which can be advantageous for the design of inhibitors. These features include a triangular shaped region which is accessible to an inhibitor. We hypothesized that molecules fitting the triangular shape of the EGF-R catalytic site which can also form favorable contacts with the hinge region of the binding site will bind more strongly and hence inhibit EGF-R more effectively. In order to elucidate the structure activity relationships determining the ability of LFM to inhibit the EGF-R tyrosine kinase as well as test the predictive value of our homology model of the EGF-R kinase domain, we have designed and synthesized analogs of this compound by systematically replacing the p-$CF_3$ substituent in the phenyl ring. Our modeling calculations were based on the homology model of the EGF-R kinase domain described above and crystal structures of the LFM and its analogs. The positions of the critical residues in the active site of the EGF-R and the docked positions of the LFM analogs are shown in FIGS. 2–3. The docked positions of the compounds indicate that the molecules maintain a close contact with the hinge region. In all cases the nitrile nitrogen of the ligand was involved in hydrogen bonding with the amide NH of Met. In modeling favorable contacts with the hinge region of the binding site would bind more strongly and hence inhibit the EGFR kinase more effectively. In modeling studies aimed at identifying LFM analogs with a high likelihood to bind favorably to the catalytic site of the EGFR kinase domain, we chose to calculate the $K_i$ values based on the binding interaction between the inhibitor and EGFR residues. The $K_i$ values were calculated for several different inhibitors and were used to rank the predicted binding strength. Each of the small molecule LFM analogs described below was individually modeled into the catalytic site of the EGFR kinase domain using an advanced docking procedure. The position of quercetin in the HCK crystal structure (Sicheri, F., et al. *Nature* 1997, 385, 602) was used as a template to obtain a reasonable starting point for the docking procedure. The various docked positions of each LFM analog was qualitatively evaluated and consequently compared with the $IC_{50}$ values of the compounds in cell-free EGFR kinase inhibition assays. Table 2 lists the interaction scores and calculated $K_i$ values for LFM and its analogs.

TABLE 2

Interaction scores, estimated $K_i$ values and measured $IC_{50}$ values for LFM analogs.

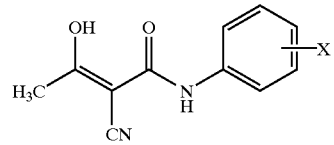

| Compound | X | HB[a] | Lipo Score | Ludi Score | Ludi[b] $K_i(\mu M)$ | EGFR Inhibition $IC_{50}(\mu M)$ | Cancer Cell Cytotoxicity $IC_{50}$ ($\mu M$) MDA-MB-231 | MDA-MB-361 |
|---|---|---|---|---|---|---|---|---|
| LFM | p-$CF_3$ | 1 | 522 | 508 | 8 | 5.4 | 198.9 | 190.5 |
| LFM-A1 | p-Br | 1 | 462 | 449 | 32 | >100 | >300 | >300 |
| LFM-A2 | p-Cl | 1 | 456 | 443 | 37 | >100 | >300 | >300 |
| LFM-A3 | p-F | 1 | 397 | 362 | >100 | >100 | >300 | >300 |
| LFM-A4 | o-$CF_3$ | 1 | 442 | 354 | >100 | >100 | >300 | >300 |
| LFM-A5 | o-Br | 1 | 424 | 383 | >100 | >100 | >300 | >300 |
| LFM-A6 | o-Cl | 1 | 385 | 345 | >100 | >100 | >300 | >300 |
| LFM-A7 | o-F | 1 | 430 | 416 | 69 | 74.5 | >300 | >300 |
| LFM-A8 | m-$CF_3$ | 1 | 492 | 465 | 22 | >100 | >300 | >300 |
| LFM-A9 | m-Br | 1 | 367 | 354 | >100 | >100 | >300 | >300 |
| LFM-A10 | m-Cl | 1 | 391 | 344 | >100 | >100 | >300 | >300 |
| LFM-A11 | m-F | 1 | 400 | 387 | >100 | >100 | >300 | >300 |
| LFM-A12 | p-$OCF_3$ | 1 | 510 | 489 | 13 | 1.7 | 53.4 | 26.3 |
| LFM-A13 | 2,5-diBr | 1 | 436 | 340 | >100 | >100 | >300 | >300 |
| LFM-A14 | none | 1 | 397 | 367 | >100 | >100 | >300 | >300 |

[a]HB = Number of hydrogen bonds.
[b]Ludi $K_i$ calculated based on the empirical score function in Ludi program(Bohm, H. J. J. Comput. Aided. Mol. Des. 1992, 6, 593; and 36. Bohm, H. J. J. Comput. Aided Mol. Des. 1994, 8, 243).
Cell-free EGF R kinase assays and MTT assays were performed as described in the Methods and the corresponding IC50 values were calculated from the dose-dependent inhibition curves.

the inhibitory activity of LFM analogs with EGF-R tyrosine kinase, we calculated the binding constants ($K_i$ values) based on the binding interaction between the compounds and the catalytic site of the EGF-R kinase domain.

EXAMPLE 3

Structure-Based Design and Synthesis of LFM Analogs Having Potent EGFR-Inhibitory Activity We hypothesized that molecules fitting the triangular shape of the EGFR catalytic site which can also form Docking Procedure and Evaluation of Protein-Inhibitor Interactions Fixed docking in the Affinity program within InsightII (InsightII, Molecular Simulations Inc. 1996, San Diego, Calif.) was used for docking the LFM analogs to the EGFR tyrosine kinase catalytic site. A triangular binding region, where the base ring of ATP can bind to EGFR, was defined using a binding sphere surface calculated by the program SPHGEN in DOCK3.5 (Kuntz, I. D., et al. *J. Mol. Biol.* 1982, 161, 269). The modeling calculations used to study the predicted binding of inhibitors to EGFR were based on the homology model of EGFR described above and the coordinates of energy-minimized models of the compounds which were used for docking. The utility of the inhibitor model coordinates were validated by their crystal structures which were obtained later and showed very similar molecular conformations. Each LFM analog was interactively docked into the triangular binding pocket of EGFR based on the position of quercetin in the HCK/quercetin crystal structure.

The hydrogens on the EGFR were generated and potentials were assigned to both receptor and ligand prior to the start of the docking procedure. The docking method in the InsightII program uses the CVFF force field and a Monte Carlo search strategy to search for and evaluate docked structures (InsighII, Molecular Simulations Inc. 1996, San Diego, Calif.). While the coordinates for the bulk of the receptor was kept fixed, the program has the ability to define a radius of residues within 5 Å distance from the LFM analog. As the modeling calculations progressed, the residues within the defined radius were allowed to shift and/or rotate to energetically favorable positions to accommodate the ligand. Calculations were carried out on an INDIGO2 computer (Silicon Graphics Inc., Mountain View, Calif.) using the CVFF force field in the Discover program and Monte Carlo search strategy in Affinity (InsighII, Molecular Simulations Inc. 1996, San Diego, Calif.). No solvation procedures were used. Conjugated gradient minimization was used to conserve CPU time, as the total number of movable atoms was greater than 200. Calculations approximating hydrophobic and hydrophilic interactions were used to determine the ten best docking positions of each LFM analog in the EGFR catalytic site. The various docked positions of each LFM analog was qualitatively evaluated using a score function in the Ludi module (Bohm, H. J. *J. Comput. Aided. Mol. Des.* 1992, 6, 593; Bohm, H. J. *J. Comput. Aided Mol. Des.* 1994, 8, 243) of the program INSIGHTII (InsighII, Molecular Simulations Inc. 1996, San Diego, Calif.) which was then used to estimate a binding constant ($K_i$) for each compound in order to rank their relative binding capabilities and predicted inhibition of EGFR. The calculated $K_i$ trends for the LFM analogs were compared with the trend of the experimentally determined tyrosine kinase inhibition as well as cytotoxicity $IC_{50}$ values for the compounds, in order to elucidate the structure-activity relationships (SAR) determining the potency of LFM analogs.

Figure 4:
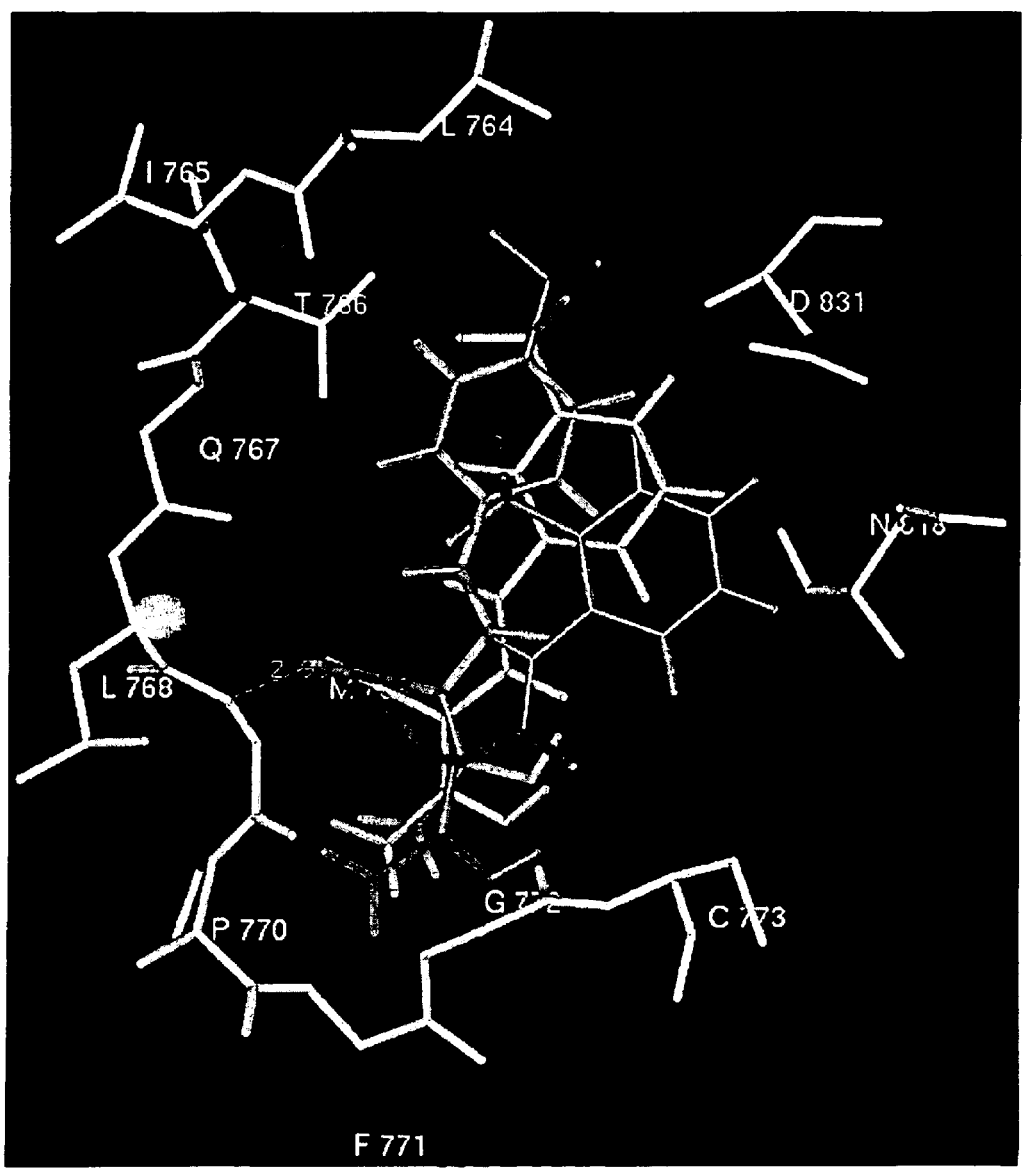
FIG. 4 shows the superimposed docked positions of $CF_3$ substituted LFM analogs in the active site of the EGFR tyrosine kinase. The residues in the active site are shown in pink. LFM: para-$CF_3$ substituted compound (active metabolite of leflunomide, green); LFM-A8: meta-$CF_3$ substituted analog (yellow); LFM-A4: ortho-$CF_3$ substituted analog (red).

The docked inhibitors were sandwiched between two regions of mostly hydrophobic residues. The region above the inhibitor consisted of residues $Leu^{694}$, $Val^{702}$, $Lys^{721}$, and $Ala^{719}$, whereas the region below included residues $Leu^{820}$ and $Thr^{830}$. The positions of the critical residues in the active site of the EGFR and the docked positions of the LFM analogs are shown in FIGS. 2–4. Of the possible orientations of the LFM analogs in this binding pocket, the one shown in FIGS. 2–4 had the highest interaction score and was assumed by all 15 compounds. This indicates that the depicted docked positions represent an energetically favored binding mode. In this binding mode the compounds can maintain close contact with the hinge region on the edge of the inhibitor, residues $Leu^{694}$ and $Val^{702}$ above the inhibitor, and $Leu^{820}$ and $Thr^{830}$ below. In all cases the nitrile nitrogen of the ligand was involved in hydrogen bonding with the amide NH of $Met^{769}$. In addition the para-substituted $OCF_3$ group appeared to form close contacts between residues $Thr^{766}$ and $Asp^{831}$.

From the modeling studies, it was apparent that ortho substitutions on the phenyl ring of LFM analogs would prevent the molecule from having close contact with the hinge region of the receptor. The poor interaction is reflected by the higher $K_i$ values calculated for this group of compounds (LFM-A4-A7; Table 2). The results indicated a trend that for a smaller substitution at the ortho position, there would be less disruption of close contacts with the receptor. As the substituted group got bulkier, the inhibitor would be pushed further away from the hinge region of the receptor, thereby weakening the contacts. The compound containing the smallest ortho-substituted group, LFM-A7 (with o-F) had the best interaction score in this group with a calculated $K_i$ of 69 μM. Docking analysis suggested that LFM-A7 had slightly increased contact with EGFR residues relative to the unsubstituted compound, LFM-A14, consistent with its lower calculated $K_i$ value.

The modeling also revealed that meta substituents, except for m-F, would likely be sandwiched between residues $Thr^{766}$ and $Asp^{831}$. The m-F group of LFM-A11 was predicted to be located on the opposite side of the molecule relative to the meta-substituted groups of the other 3 compounds, and docking showed that the m-F group of LFM-A11 would be located near $Asn^{818}$, instead of the usual binding mode where the meta group is located between $Thr^{766}$ and $Asp^{831}$, opposite $Asn^{818}$. The calculated $K_i$ values for compounds with m-F, m-Cl and m-Br substitutions were greater than 100 μM (Table 2). The results shown in Table 2 indicate that LFM-A8, which has a m-$CF_3$ substitution, is the best fitting compound in this group with a calculated $K_i$ of 22 μM. While maintaining the close contact with the hinge region, the m-$CF_3$ substituent of LFM-A8 would extend further into a leucine-rich pocket of the protein (beyond $Thr^{766}$ and $Asp^{831}$) and gain more hydrophobic contact. Consequently, LFM-A8 was predicted to bind to the catalytic site of the EGFR kinase domain better than the other meta-substituted LFM analogs.

The modeling also revealed that the LFM analogs with para substitutions would have the greatest potential for inhibition of the EGFR, with p-$CF_3$ and p-$OCF_3$ being the most promising (calculated $K_i \sim$ 8–13 μM), followed by p-Cl and p-Br, (calculated $K_i \sim$ 30–40 μM), and p-F (calculated $K_i >$ 100 μM) (Table 2). The best docked positions of the five para substituted compounds showed a binding pattern similar to that of the meta substituted compounds except for a slight shift of the phenyl rings toward $Thr^{766}$ (FIG. 3). The para substituted compounds would maintain a close contact with the hinge region of the EGFR kinase domain and be stabilized by additional contact area between the para substituents and the residues deep inside the binding site. The $CF_3$ and $OCF_3$ substituents in the para position would extend toward the deepest corner of the binding site which would result in improved molecular contact. For compound LFM-A3, the C-F bond length (1.3 Å) is shorter than the C—Cl and C—Br bond lengths in LFM-A2 and LFM-A1 (1.8–1.9 Å) and thus the p-F group would not approach $Lys^{721}$ as closely. This weaker contact may contribute to the poor $K_i$ values for LFM-A3. The para substituted compounds appeared to approach $Asp^{831}$ of EGFR more closely compared to ortho or meta substituted compounds. The result of this closer approach may be some steric strain with $Asp^{831}$ which may force the residue to rotate away from the inhibitor as was observed in docking results. This action actually disrupts a hydrogen bond between $Asp^{831}$ and $Asn^{830}$ which could cause a slight destabilization of the protein conformation in this region. This event is more likely to occur when larger para-substituted groups are involved, such as the para-Br of LFM-A1 and para-Cl of LFM-A2. The calculations did not incorporate the energetic effects of this speculated protein destabilization. Therefore, the true $K_i$ values for compounds containing a larger para-substituted group, such as LFM-A1 and LFM-A2, may be higher than the estimated $K_i$ values shown in Table 2.

In these studies, the para substituted $CF_3$ was more active than the m-$CF_3$ compound in terms of $IC_{50}$ inhibition values ($IC_{50}$=5.4 μM vs>100 μM, Table 1), which is consistent with the modeling observation that this compound maintains closer contacts with the hinge region than the m-$CF_3$ compound. As shown in FIG. 3, the meta substitution is sterically less favorable for allowing a closer interaction with the hinge region of EGF-R relative to para substituted LFM compounds, which may contribute to a loss of hydrophobic contact in this region of the binding site. This loss of hydrophobic contact would be reflected in a lower calculated $K_i$ value based on docking studies.

The superimposed docked positions of the three $CF_3$ substituted compounds (ortho, meta, and para) are shown in FIG. 4. The bulky ortho substitution would prevent the ligands from having close contact with the catalytic site and make it unlikely for this compound to show significant inhibitory activity. The para substituted compound, on the other hand, can maintain good contact with the hinge region of the receptor and would likely be an effective inhibitor by our calculations. The inhibition values for meta substituted compounds were predicted to fall between those of the ortho and para substituted compounds. The calculated $K_i$ values are consistent with their final docked positions which show that the m-$CF_3$ compound is located in-between the para and ortho compounds. Docking studies also showed that the ring substituents of most of the active compounds were predicted to be positioned between residues $Thr^{766}$ and $Asp^{831}$ of the EGFR.

The modeling studies suggested that LFM-A12 would exhibit potent EGFR-inhibitory activity. In order to test this hypothesis and validate the predictive value of the described EGFR kinase domain homology model, LFM-A12, LFM, and 13 other LFM analogs listed in Table 2 were prepared. The three dimensional structures of 10 of these compounds were determined by single crystal X-ray diffraction. The crystal data, experimental parameters and refinement statistics are summarized in Table 1. All structures, except LFM-A2 (p-Cl), were found to be essentially planar in conformation, and all bond lengths and angles were in the expected range. For LFM-A2 the dihedral angle between the aromatic ring and side chain was close to 45°.

In all crystal structures except LFM-A 11 (m-F-), the ortho or meta substituents were found to reside on the same side of the molecule as the nitrile group. In LFM-A11, the phenyl ring is rotated so that the meta-F and nitrile groups are on opposite sides of the molecule. The molecular coordinates of LFM and LFM analogs which were energy-minimized and docked into the EGFR binding site in modeling studies adopted a conformation similar to that of their crystal structures.

The effects of a compound on EGFR tyrosine kinase and survival of human breast cancer cells can be determined using pharmacological models which are well known to the art, or using the biological tests described below.

EXAMPLE 4

Chemistry and Synthesis

All chemicals were purchased from Aldrich (Milwaukee, Wis.) and were used without further purification. Except where noted, each reaction vessel was secured with a rubber septum, and the reaction was performed under nitrogen atmosphere. $^1H$ spectra were obtained on a Varian Mercury 300 instrument spectrometer (Palo Alto, Calif.) at ambient temperature in the solvent specified. Melting points were determined using a Fisher-Johns melting point apparatus and are uncorrected. FT-IR spectra were recorded on a Nicolet Protege 460 spectrometer (Madison, Wis.). GC/MS spectra were obtained on a HP 6890 GC System (Palo Alto, Calif.) equipped with a HP 5973 Mass Selective Detector.

Scheme 1 shows the general synthetic scheme for the preparations of LFM, and LFM-A1-LFM-A14 (Kuo, E. A., et al. *J. Med. Chem.* 1996, 39, 4608; Sjogren, E. R., et al. *J. Med. Chem.* 1991, 34, 3295). Cyanoacetic acid 1 was coupled with the REQUISITE substituted-aniline 2 in the presence of diisopropylcarbodiimide (DIC) to form 3. Compound 3 was treated with NaH and acylated with acetyl chloride to afford the final products.

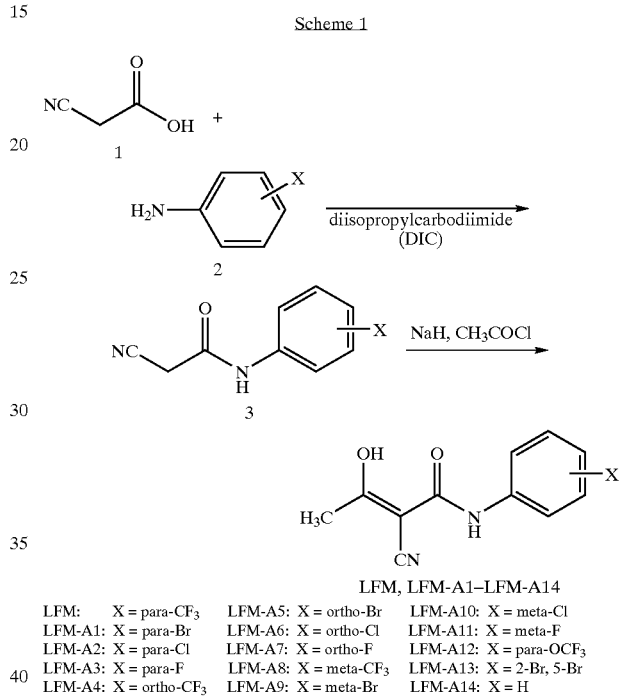

Scheme 1

LFM, LFM-A1–LFM-A14
LFM:    X = para-$CF_3$      LFM-A5: X = ortho-Br      LFM-A10: X = meta-Cl
LFM-A1: X = para-Br         LFM-A6: X = ortho-Cl      LFM-A11: X = meta-F
LFM-A2: X = para-Cl         LFM-A7: X = ortho-F       LFM-A12: X = para-$OCF_3$
LFM-A3: X = para-F          LFM-A8: X = meta-$CF_3$   LFM-A13: X = 2-Br, 5-Br
LFM-A4: X = ortho-$CF_3$    LFM-A9: X = meta-Br       LFM-A14: X = H General Synthetic Procedures The general synthetic procedures are described in the literature. (Kuo, E. A., et al. *J. Med. Chem.* 1996, 39, 4608; Sjogren, E. R., et al. *J. Med. Chem.* 1991, 34, 3295). In general, 1,3-diisopropylcarbodiimide (1.75 g; 13.9 mmol) was added to a solution of cyanoacetic acid 1 (1.70 g; 20.0 mmol) and the requisite substituted-aniline 2 (12.6 mmol) in tetrahydrofuran (25 mL) at 0° C. The mixture was stirred for 12 hours at room temperature.

The urea precipitate (reaction side product) was removed by filtration and the filtrate was partitioned between ethyl acetate and 0.5 N HCl. The organic layer was sequentially washed with brine twice, dried over anhydrous $Na_2SO_4$ and concentrated by rotary-evaporation. The solid product was recrystallized from ethyl alcohol to give pure 3. Sodium hydride (0.93 g; 60% in mineral oil; 23.2 mmol) was added slowly to the solution of 3 (12.0 m mol) in tetrahydrofuran (40 mL) at 0° C. After stirring for 30 minutes at 0° C., the requsite acid chloride $R_1COCl$ (1.04 g; 13.2 mmol) was added to the reaction mixture. The reaction was continued for another hour at room temperature and then was quenched by the addition of acetic acid (2 mL). The mixture was poured into ice water (100 mL) containing 2.5 mL of hydrochloric acid to precipitate the crude product, which was collected by filtration and washed with water. The final pure product was obtained by recrystallization.

Physical Data of Specific Compounds:

α-Cyano-β-hydroxy-β-methyl-N-[4-(trifluoromethyl)phenyl]-propenamide (LFM). mp: 230–233° C.; IR (KBr): 3303, 2218, 1600 and 1555 cm$^{-1}$; $^1$H NMR (DMSO-d$_6$): δ 11.01 (s, 1H, NH), 7.75 (d, J=8.4 Hz, 2H, ArH), 7.64 (d, J=8.4 Hz, 2H, ArH), 2.22 (s, 3H, CH$_3$); GC/MS m/z 270 (M$^+$), 161, 142, 111.

α-Cyano-β-hydroxy-β-methyl-N-(4-bromophenyl)propenamide (LFM-A1). mp: 213–214° C.; IR (KBr): 3288, 2228, 1615, 1555 cm$^{-1}$; $^1$H NMR (DMSO-d$_6$): δ 10.51 (s, 1H, NH), 7.49 (s, 4H, ArH), 2.25 (s, 3H, CH$_3$); MS (EI) m/z 282(M$^+$+z), 280 (M$^+$), 173, 171.

α-Cyano-β-hydroxy-β-methyl-N-(4-chlorophenyl)propenamide (LFM-A2). mp: 209–211° C.; IR(KBr): 3298, 2223, 1598 and 1552 cm$^{-1}$; $^1$H NMR (DMSO-d$_6$): δ 10.48 (s, 1H, NH), 7.54 (d, J=8.7 Hz, 2H, ArH), 7.45 (s br, 1H, OH), 7.36 (d, J=8.7 Hz, 2H, ArH), 2.25 (s, 3H, CH$_3$); MS (CI) m/z 236 (M$^+$), 121, 127.

α-Cyano-β-hydroxy-β-methyl-N-(4-fluorophenyl)propenamide (LFM-A3). mp: 165–166° C.; IR (KBr): 3298, 2218, 1610 and 1560 cm$^{-1}$; $^1$H NMR (DMSO-d$_6$): δ 10.33 (s, 1H, NH), 7.80 (s br, 1H, OH), 7.53 (m, 2H, ArH), 7.16 (m, 2H, ArH), 2.26 (s, 3H, CH$_3$); GC/MS m/z 220 (M$^+$), 111.

α-Cyano-β-hydroxy-β-methyl-N-[2-(trifluoromethyl)phenyl]-propenamide (LFM-A4). mp: 61–63° C.; IR (KBr): 3435, 2209, 1619, 1952 and 1548 cm$^{-1}$; $^1$H NMR (DMSO-d$_6$): δ 10.99 (s, 1H, NH), 8.03 (d, J=7.5 Hz, 1H, ArH), 7.67 (d, J=7.5 Hz, 1H ArH), 7.60 (dd, J=7.5, 7.5 Hz, 1H, ArH), 7.29 (dd, J=7.5, 7.5 Hz, 1H, ArH) 5.71 (s br, 1H OH), 2.20 (s, 3H, CH$_3$); GC/MS m/z 270 (M$^+$), 161, 141, 114.

α-Cyano-β-hydroxy-β-methyl-N-(2-bromophenyl)propenamide (LFM-A5). mp: 98–100° C.; IR (KBr): 3351, 2214, 1609, 1585 and 1536 cm$^{-1}$; $^1$H NMR (DMSO-d$_6$): δ 10.76 (s, 1H, NH), 8.06 (dd, J=8.1, 1.5 Hz, 1H, ArH), 7.62 (dd, J=8.1, 1.5 Hz, 1H, ArH), 7.33 (m, 1H, ArH), 7.03 (m, 1H, ArH), 6.60 (s br, 1H, OH), 2.22 (s, 3H, CH$_3$); ); MS (EI) m/z 282(M$^+$+z), 280 (M$^+$), 173, 171.

α-Cyano-β-hydroxy-β-methyl-N-(2-chlorophenyl)propenamide (LFM-A6). mp: 93–94° C.; IR (KBr): 3372, 2208, 1644, 1621 and 1587 cm$^{-1}$; $^1$H NMR (DMSO-d$_6$): δ 10.96 (s, 1H, NH), 8.16 (d, J=8.1 Hz, 1H, ArH), 7.46 (dd, J=7.5, 1.5 Hz, 1H, ArH), 7.29 (m, 1H, ArH), 7.08 (m, 1H, ArH), 2.22 (s, 3H, CH$_3$); MS (CI) m/z 236 (M$^+$), 29, 127.

α-Cyano-β-hydroxy-β-methyl-N-(2-fluorophenyl)propenamide (LFM-A7). mp: 118–119° C.; IR (KBr): 3409, 2212, 1613, 1591 and 1532 cm$^{-1}$; $^1$H NMR (DMSO-d$_6$): δ 10.70 (s, 1H, NH), 7.91 (m, 1H, ArH), 7.23 (M, IH, ArH), 7.13 (m, 2H, ArH), 7.10 (s br, 1H, OH), 2.22 (s, 3H, CH$_3$); GL/MS m/z 220 (M$^+$), 111.

α-Cyano-β-hydroxy-β-methyl-N-[3-(trifluoromethyl)phenyl]-propenamide (LFM-A8). mp: 182–184° C.; IR (KBr): 3303, 2221, 1619 and 1572 cm$^{-1}$; $^1$H NMR (DMSO-d$_6$): δ 10.79 (s, 1H, NH), 8.05 (s br, 1H, OH) 8.04 (s, 1H, ArH), 7.75 (d, J=8.1 Hz, 1H, ArH), 7.53 (dd, J=8.1, 7.5 Hz, 1H, ArH), 7.42 (d, J=7.5 Hz, 1H, ArH), 2.24 (s, 3H, CH$_3$); GL/MS m/z 270 (M$^+$), 161.

α-Cyano-β-hydroxy-β-methyl-N-(3-bromophenyl)propenamide (LFM-A9). mp: 184–185° C.; IR (KBr): 3303, 2228, 1610, 1595 and 1550 cm$^{-1}$; $^1$H NMR (DMSO-d$_6$): δ 10.56 (s, 1H, NH), 7.89 (m, 1H, ArH), 7.47 (m, 1H, ArH), 7.28 (m, 2H, ArH), 6.37 (s br, 1H, OH), 2.26 (s, 3H, CH$_3$); MS (EI) m/z 282 (M$^+$+H, $^{81}$Br), 280 (M$^+$+H, $^{79}$Br), 171, 173.

α-Cyano-β-hydroxy-β-methyl-N-(3-chlorophenyl)propenamide (LFM-A10). mp: 184–187° C.; IR (KBr): 3293, 2221, 1610, 1595 and 1557 cm$^{-1}$; $^1$H NMR (DMSO-d$_6$): δ 10.61 (s, 1H, NH), 7.76 (m, 1H, ArH), 7.42 (m, 1H, ArH), 7.33 (M, 1H, ArH), 7.16 (m, 1H, ArH), 6.84 (S br, 1H, OH), 2.25 (s, 3H, CH$_3$); MS (CI) m/z 236 (M$^+$).

α-Cyano-β-hydroxy-β-methyl-N-(3-fluorophenyl)propenamide (LFM-A11). mp: 136–138° C.; IR (KBr): 3297, 2221, 1613, 1597 and 1567 cm$^{-1}$; $^1$H NMR (DMSO-d$_6$): δ 10.54 (s, 1H, NH), 7.54 (m, 1H, ArH), 7.33 (m, 2H, ArH), 6.93 (m, 1H, ArH), 2.27 (s, 3H, CH$_3$); GL/MS m/z 220 (M$^+$), 111.

α-Cyano-β-hydroxy-β-methyl-N-[4-(trifluoromethoxy)phenyl]-propenamide (LFM-A12). mp: 182–183° C.; IR (KBr): 3308, 2213, 1625 and 1580 cm$^{-1}$; $^1$H NMR (DMSO-d$_6$): δ 10.57 (s, 1H, NH), 7.90 (s br, 1H, OH), 7.64 (d, J=8.7 Hz, 2H, ArH), 7.32 (d, J=8.7 Hz, 2H, ArH), 2.25 (s, 3H, CH$_3$); GL/MS m/z 286 (M$^+$), 177, 108.

α-Cyano-β-hydroxy-β-methyl-N-(2,5-dibromophenyl)propenamide (LFM-A13). mp: 148–150° C.; IR (KBr): 3353, 2211, 1648 and 1590 cm$^{-1}$; $^1$H NMR (DMSO-d$_6$): δ 11.41 (s, 1H, NH), 8.57 (d, J=2.4 Hz, 1H, ArH), 7.55 (d, J=8.7 Hz, 1H, ArH), 7.14 (dd, J=8.7, 2.4 Hz, 1H, ArH), 7.10 (s br, 1H, OH), 2.17 (s, 3H, CH$_3$); MS (EI) m/z 362 (M$^+$+4), 360 (M$^+$+2), 358 (M$^+$), 253, 251, 249, 150.

α-Cyano-β-hydroxy-β-methyl-N-(phenyl)propenamide (LFM-A14). mp: 134–135° C.; IR (KBr): 3281, 2214, 1605, 1579 and 1554 cm$^{-1}$; $^1$H NMR (DMSO-d$_6$): δ 10.33 (s, 1H, NH), 7.51 (d, J=7.5 Hz, 2H, ArH), 7.40 (s br, 1H, OH), 7.31 (dd, J=7.5, 7.5 Hz, 2H, ArH), 7.11 (m, 1H, ArH), 2.26 (s, 3H, CH$_3$); GL/MS m/z 202 (M$^+$), 93.

EXAMPLE 5

Biological Tests

Immunoprecipitation of Recombinant Proteins from Insect Cells

Sf21 cells were infected with a baculovirus expression vector for BTK, JAK1, or JAK3, as previously reported (Vassilev, A., et al. *J. Biol. Chem.* 1998, 274, 1646–1656; Goodman, P. A., et al. *J. Biol. Chem.* 1998, 273, 17742). Cells were harvested and lysed (10 mM Tris pH 7.6, 100 mM NaCl, 1% Nonidet P-40, 10% glycerol, 50 mM NaF, 100 mM Na$_3$VO$_4$, 50 mg/ml phenylmethylsulfonyl fluoride, 10 mg/ml aprotonin, 10 mg/ml leupeptin) and the kinases were immunoprecipitated from the lysates, as reported (Vassilev, A., et al. *J. Biol. Chem.* 1998, 274, 1646–1656).

Antibodies used for immunoprecipitations from insect cells are as follows: Polyclonal rabbit anti-BTK serum (Mahajan, S., et al. *Mol. Cell. Biol.* 1995, 15, 5304), polyclonal rabbit anti-JAK1 (HR-785), cat# sc-277, rabbit polyclonal IgG affinity purified, 0.1 mg/ml, Santa Cruz Biotechnology; and polyclonal rabbit anti-JAK3 (C-21, cat # sc-513, rabbit polyclonal IgG affinity purified, 0.2 mg/ml, Santa Cruz Biotechnology). Kinase assays were performed following a 1 hour exposure of the immunoprecipitated tyrosine kinases to the test compounds, as described in detail elsewhere (Mahajan, S., et al. *Mol. Cell. Biol.* 1995, 15, 5304; Uckun, F. M., et al. *Science* 1996, 22, 1096). The immunoprecipitates were subjected to Western blot analysis as previously described (Vassilev, A., et al. *J. Biol. Chem.* 1998, in press).

Cell Lines, Reagents, and Biochemical Assays:

MDA-MB-231 (ATCC HTB-26) and MDA-MB-361 (ATCC HTB-27) are EGFR positive human breast cancer cell lines (Uckun, F. M., et al. *Clin. Can. Res.* 1998, 4, 901). These cell lines were maintained in RPMI 1640 medium supplemented with 10% fetal bovine serum. For subculturing, medium was removed from the flasks containing a confluent layer of cells, and fresh 0.25% trypsin was added for 1–2 min. Trypsin was removed and cultures incubated for 5–10 min. at 37° C. until cells detached. Fresh medium was then added, and cells were aspirated and dispensed into new flasks. COS-7 simian kidney cell line and HepG2 human hepatoma cell line were obtained from ATCC.

Antibodies directed against BTK, JAK1, JAK3, and HCK have been described previously (Vassilev, A., et al. *J. Biol. Chem.* 1998, in press; Goodman, P. A., et al. *J. Biol. Chem.* 1998, 273, 17742; Mahajan, S., et al. *Mol. Cell. Biol.* 1995, 15, 5304; Uckun, F. M., et al. *Science* 1996, 22, 1096). Polyclonal antibodies to BTK were generated by immunization of rabbits with glutathione S-transferase (GST) fusion proteins (Pharmacia Biotech Inc.) containing the first 150 amino acids of BTK. The monoclonal anti-Fas antibody (F22120) was obtained from the Transduction Laboratories, Inc. (Lexington, Ky.).

Immunoprecipitations, immune-complex protein kinase assays, and immunoblotting using the ECL chemiluminescence detection system (Amersham Life Sciences) were conducted as described previously (Vassilev, A., et al. *J. Biol. Chem.* 1998, in press; Goodman, P. A., et al. *J. Biol. Chem.* 1998, 273, 17742; Mahajan, S., et al. *Mol. Cell. Biol.* 1995, 15, 5304; Uckun, F. M., et al. *Science* 1996, 22, 1096).

Horse radish peroxidase-conjugated sheep anti-mouse, donkey anti-rabbit secondary antibodies and ECL reagents were purchased from Amersham (Oakbrook, Ill.). For insulin receptor kinase (IRK) assays, HepG2 human hepatoma cells grown to approximately 80% confluency were washed once with serum-free DMEM and starved for 3 hour at 37° in a $CO_2$ incubator. Subsequently, cells were stimulated with insulin (Eli Lilly, cat# CP-410;10 units/ml/$10 \times 10^6$ cells) for 10 minutes at room temperature. Following this IRK activation step, cells were washed once with serum free medium, lysed in NP-40 buffer and IRK was immunoprecipitated from the lysates with an anti-IRb antibody (Santa Cruz, Cat.# sc-711, polyclonal IgG). Prior to performing the immunecomplex kinase assays, the beads were equilibrated with the kinase buffer (30 mM Hepes pH 7.4, 30 mM NaCl, 8 mM MgCl2, 4 mM $MnCl_2$).

For HCK kinase assays, we used HCK-transfected COS-7 cells. The cloning and expression of HCK in COS-7 cells has been described previously (Saouaf, S. J., et al. *J. Biol. Chem.* 1995, 270, 27072). The pSV7c-HCK plasmid was transfected into $2 \times 10^6$ COS-7 cells using Lipofectamine (GIBCO/BRL), and the cells were harvested 48 hours later. The cells were lysed in NP-40 buffer and HCK was immunoprecipitated from the whole cell lysates with an anti-HCK antibody.

Immune-Complex Kinase Assays and Anti-Phosphotyrosine Immunoblotting:

For EGFR immune complex kinase assays, 24-hours after treatment with leflunomide analogs, MDA-MB-231 breast cancer cells were stimulated with 20 ng/mL EGF for 5 minutes, lysed in 1% Nonidet-P-40 buffer, and cell lysates were immunoprecipitated with an anti-EGFR antibody reactive with the sequence $Ala^{351}$-$Asp^{364}$ of the human EGFR (Upstate Biotechnology Inc. [UBI] Catalog # 05-104) (Uckun, F. M., et al. *Clin. Can. Res.* 1998, 4, 901). EGFR immune complexes were examined for tyrosine phosphorylation by Western blot analysis, as described by Uckun, F. M., et al. *Clin. Can. Res.* 1998, 4, 901. All anti-phosphotyrosine Western blots were subjected to densitometric scanning using the automated AMBIS system (Automated Microbiology System, Inc., San Diego, Calif.) and for each time point a % inhibition value was determined by comparing the density ratios of the tyrosine phosphorylated EGFR protein bands to those of the baseline sample and using the formula: % Inhibition=100–100×[Density of tyrosine phosphorylated EGFR band]$_{test\ sample}$/[Density of tyrosine phosphorylated EGFR band]$_{baseline\ control\ sample}$. The $IC_{50}$ values were determined using an Inplot program (Graphpad Software, Inc., San Diego, Calif.).

In other experiments, MDA-MB-231 cells were stimulated with 10 ng/ml EGF prior to immunoprecipitation of the EGFR. EGFR immune complexes were incubated for 1 hour at room temperature with various LFM analogs and tyrosine kinase assays were performed in the presence of [$\gamma$-$^{32}$P]-ATP, as previously described (Uckun, F. M., et al. *Clin. Can. Res.* 1998, 4, 901; Narla, R. K., et al. *Clin. Can. Res* 1998, 1405; Uckun, F. M., et al. *Science* 1996, 22, 1096; Uckun, F. M., et al. *Science* 1995, 267, 886). The kinase assay gels were analyzed both by autoradiography and using the Bio-Rad Storage Phosphor Imager System (BioRad, Hercules, Calif.) for quantitative scanning.

In Vitro Treatment of Cells with LFM Compounds:

In order to determine the cytotoxic activity of LFM and its analogs against breast cancer cells, cells in alpha-MEM supplemented with 10% (v/v) fetal calf serum were treated with various concentrations of the compounds for 24 hours at 37° C., washed twice in alpha-MEM, and then used in either MTT assays or in vitro invasion assays, as described hereinafter.

Cytotoxicity Assay:

The cytotoxicity of various compounds against human breast cancer cell lines was analyzed using the MTT (3-[4, 5-dimethylthiazol-2-yl]-2,5-diphenyl tetrazolium bromide) assay (Boehringer Mannheim Corp., Indianapolis, Ind.). Uckun F. M., et al. *Clin. Cancer Res.* 1998, 4, 901–912. Exponentially growing breast cancer cells were seeded into a 96-well plate at a density of $2.5 \times 10^4$ cells/well and incubated for 36 hours at 37° C. prior to drug exposure. On the day of treatment, culture medium was carefully aspirated from the wells and replaced with fresh medium containing the LFM analogs at concentrations ranging from 2 to 250 $\mu$M. Triplicate wells were used for each treatment. The cells were incubated with the various compounds for 36 hours at 37° C. in a humidified 5% $CO_2$ atmosphere. To each well, 10 $\mu$l of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems) at 540 nm and a reference wavelength of 690 nm.

To translate the absorbance $A_{540}$ values into the number of live cells in each well, the $A_{540}$ values were compared to those on standard $A_{540}$-versus-cell number curves generated for each cell line. The percent survival was calculated using the formula: % survival=Live cell number[test]/Live cell number [control]×100. The $IC_{50}$ values were calculated by non-linear regression analysis using an Graphpad Prism software version 2.0 (Graphpad Software, Inc., San Diego, Calif.).

Confocal Laser Scanning Microscopy:

Immunofluorescence was used to examine the morphologic features of breast cancer cells treated with LFM and its analogs. Before the experiment, cells were trypsinized from rapidly growing tissue culture flasks and seeded onto sterile 22 mm$^2$ coverslips in 6-well culture plates. Cells on coverslips were returned to the incubator for 24 hours prior to treatment. The following day, drugs were added from a stock solution made in DMSO to a final concentration of 100 μM. Final DMSO concentration was 0.1% in both test samples and controls. Cells were returned to a 37° C. incubator for 24 hours before further processing.

At 24 hours, coverslips were fixed in −20° C. methanol for 15 minutes followed by a 15 minute incubation in phosphate buffered saline +0.1% Triton X-100(PBS-Tx). Coverslips were next incubated with a monoclonal antibody against α-tubulin (Sigma Chemical Co, St. Louis, Mo.) at a dilution of 1:1000 for 40 minutes in a humidified chamber at 37° C. Coverslips were washed for 15 minutes in PBS-Tx followed by a 40 min incubation with a goat anti-mouse IgG antibody conjugated to FITC (Amersham Corp., Arlington Heights, Ill.). The coverslips were again rinsed in PBS-Tx and incubated with 5 μM TOTO-3 (Molecular Probes, Eugene Oreg.) for 20 minutes to label the nuclear DNA. Coverslips were immediately inverted onto slides in Vectashield (Vector Labs, Burlingame) to prevent photobleaching, sealed with nail varnish and stored at 4° C. Slides were examined using a Bio-Rad MRC-1024 Laser Scanning Confocal Microscope mounted on a Nikon Eclipse E800 upright microscope with high numerical aperture objectives. Digital data was processed using Lasersharp (Bio-Rad, Hercules Calif.) and Adobe Photoshop softwares (Adobe Systems, Mountain View, Calif.) and printed on a Fuji Pictography thermal transfer printer (Fuji, Elmsford, N.Y.).

Apoptosis Assays:

Loose packing of membrane phospholipid head groups and cell shrinkage precede DNA fragmentation in apoptotic cells, thereby providing MC540 binding as an early marker for apoptosis (Uckun F. M., et al. Clin. Cancer Res. 1998, 4, 901–912; and Kuo, E. A. J. Med. Chem. 1996, 39, 4608–4621). Plasma membrane permeability to propidium iodide (PI, Sigma) develops at a later stage of apoptosis (Uckun F. M., et al. Clin. Cancer Res. 1998, 4, 901–912; and Kuo, E. A. J. Med. Chem. 1996, 39, 4608–4621). MC540 binding and PI permeability were simultaneously measured in breast cancer cells 24 hours after exposure to leflunomide analogs, as described (Uckun F. M., et al. Clin. Cancer Res. 1998, 4, 901–912. Stock solutions of MC540 and PI, each at 1 mg/mL, were passed through a 0.22 μm filter and stored at 4° C. in the dark. Shortly before analysis, suspensions containing 1×10$^6$ cells were suspended in 5 μg/mL MC540 and 10 μg/mL PI and kept in the dark at 4° C. Whole cells were analyzed with a FACS Calibur or FACS Vantage flow cytometer (Becton Dickinson, San Jose, Calif.). All analyses were done using 488 nm excitation from an argon laser. MC540 and PI emissions were split with a 600 nm short pass dichroic mirror and a 575 nm band pass filter was placed in front of one photomultiplier tube to measure MC540 emission and a 635 nm band pass filter was used for PI emission.

Clonogenic Assays:

After treatment with LFM analogs, cells were resuspended in clonogenic medium consisting of alpha-MEM supplemented with 0.9% methylcellulose, 30% fetal bovine serum, and 50 μM 2-mercaptoethanol. Cells were plated in duplicate Petri dishes at 100,000 cells/mL/dish and cultured in a humidified 5% CO2 incubator for 7 days. Cancer cell colonies were enumerated on a grid using an inverted phase microscope of high optical resolution (Uckun F. M., et al. Clin. Cancer Res. 1998, 4, 901–912; and Kuo). Results were expressed as % inhibition of clonogenic cells at a particular concentration of the test agent using the formula: % Inhibition=(1-Mean # of colonies [Test]/Mean # of colonies [Control])×100. Furthermore, the dose survival curves were constructed using the percent control survival (=Mean # of colonies[Test]/Mean # of colonies [Control]×100) results for each drug concentration as the data points and the IC50 values were calculated. The IC50 values were determined using an Prism Version II Inplot program (Graphpad Software, Inc., San Diego, Calif.).

Transfilter Cell Invasion Assays:

The in vitro invasiveness of MDA-MB-231 human breast cancer cells was assayed using a previously published method, which employs Matrigel-coated Costar 24-well transwell cell culture chambers ("Boyden chambers") with 8.0 μm pore polycarbonate filter inserts which have been demonstrated to permit the migration of human cancer cells (Yoshida, D., et al. Neurosurgery 1996, 39, 360). The chamber filters were coated with 50 μg/ml of Matrigel matrix, incubated overnight at room temperature under a laminar flow hood and stored at 4° C.

On the day of the experiment, the coated inserts were rehydrated with 0.5 ml serum-free DMEM containing 0.1% bovine serum albumin for 1–2 hours. To study the effects of LFM and LFM-A12 on invasiveness of MDA-MB-231 cells, exponentially growing cells were incubated with each compound at various concentrations ranging from 12.5 RM to 100 μM in 0.1% DMSO overnight. The cells were trypsinized, washed twice with serum-free DMEM containing BSA, counted and resuspended at 1×10$^5$ cells/ml.

A 0.5 ml cell suspension containing 5×10$^4$ cells in a serum-free DMEM containing LFM, LFM-A12, or vehicle was added to the Matrigel-coated and rehydrated filter inserts. Next, 750 μl of NIH fibroblast conditioned medium was placed as a chemoattractant in 24-well plates and the inserts were placed in wells and incubated at 37° C. for 48 hours. After the incubation period, the filter inserts were removed, the medium was decanted off and the cells on the top side of the filter that did not migrate were scraped off with a cotton-tipped applicator. The invasive cells that migrated to the lower side of the filter were fixed, stained with Hema-3 solutions and counted under microscope. No cells were detected at the bottom of the Boyden chambers. Therefore, the number of cells on the lower side of the filters accounted for all cells that had migrated through the filter. Five (5) to ten (10) random fields per filter were counted to determine the mean (±SE) values for the invasive fraction. The invasive fractions of cells treated with LFM or LFM-A12 were compared to those of vehicle (0.1% DMSO in PBS) treated control cells and the percent inhibition of invasiveness was determined using the following formula: % Inhibition=100×(1-Invasive Fraction of Drug-Treated Cells/Invasive Fraction of Control Cells).

Results

Specific Inhibition of the EGFR Tyrosine Kinase by LFM-A12:

The effects of LFM analogs on the enzymatic activity of the EGFR kinase in cell-free immune complex kinase assays were examined. As shown in FIG. 5A, a one hour incubation with LFM or LFM-A12 inhibited the EGFR tyrosine kinase in a dose-dependent fashion in anti-EGFR immunoprecipitates from lysates of MDA-MB-231 human breast cancer cells. The $IC_{50}$ values for EGFR inhibition were 5.4 μM for LFM and 1.7 μM for LFM-A12 (FIG. 5A). In contrast, the $IC_{50}$ values for all other compounds were >100 μM, except for LFM-A7 which was 74.5 μM.

The effects of LFM and LFM analogs on the enzymatic activity of the EGFR tyrosine kinase in breast cancer cells were also examined. After a 24 hour exposure to LFM or LFM analogs, MDA-MB-231 cells were stimulated with EGF for 10 minutes, and EGFR immune complexes from whole cell lysates were subjected to Western blot analysis with a polyclonal anti-phosphotyrosine antibody to measure the autophosphorylation of the EGFR. Treatment of MDA-MB-231 cells with LFM-A12 and, albeit to a lesser extent, with LFM resulted in decreased tyrosine phosphorylation of the EGFR after EGF stimulation. In contrast, none of the other LFM analogs tested side-by-side were able to inhibit the EGFR kinase in cell-free (Table 2) or cellular (not shown) EGFR kinase inhibition assays. Taken together, these experimental results are consistent with the general trend for most of the calculated $K_i$ values shown in Table 2, thereby confirming the predictive value of the constructed homology model of the EGFR kinase domain.

In MTT assays (Uckun, F. M., et al. *Clin. Can. Res.* 1998, 4, 901; Narla, R. K., et al. *Clin. Can. Res* 1998, 1405), LFM-A12 exhibited significant cytotoxicity against the MDA-MB-361 human breast cancer cell line with mean $IC_{50}$ value of 26.3 μM. By comparison, LFM was significantly less active against these breast cancer cells. The $IC_{50}$ value for the LFM composite dose survival curves was 190.5 μM for MDA-MB-361 cells.

The inhibitory effects of LFM and LFM-A12 on the EGFR tyrosine kinase were specific in that they did not affect the enzymatic activity of other protein tyrosine kinases, including receptor family tyrosine kinase IRK (FIG. 7B), Src family tyrosine kinase HCK (FIG. 7C), Janus kinases JAK1 and JAK3 (FIGS. 7D–E), and Tec family tyrosine kinase BTK (FIG. 7F), at concentrations as high as 350 μM (Table 3).

TABLE 3

LFM-A12 interaction scores, calculated $K_i$ values and measured $IC_{50}$ values for the inhibition of several protein tyrosine kinases.

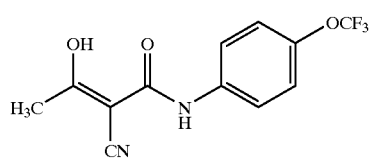

| Protein | HB[a] | Lipo Score | Ludi Score | Ludi[b] $K_i$(μM) | Inhibition $IC_{50}$(μM) |
|---|---|---|---|---|---|
| EGFR | 1 | 510 | 489 | 13 | 1.7 |
| BTK  | 1 | 496 | 457 | 27 | >175 |
| IRK  | 1 | 451 | 411 | 78 | >350 |
| HCK  | 0 | 510 | 385 | 142 | >350 |
| JAK1 | 1 | 387 | 347 | 340 | >175 |
| JAK3 | 0 | 402 | 277 | 1710 | >350 |

[a]HB = Number of hydrogen bonds between inhibitor and protein.
[b]Ludi $K_i$ calculated based on the empirical score function in Ludi program (Bohm, H. J. J. Comput. Aided. Mol. Des. 1992, 6, 593; and 36. Bohm, H. J. J. Comput. Aided Mol. Des. 1994, 8, 243).
Cell-free tyrosine kinase inhibition assays were performed as described above and the IC50 values were calculated from the LFM-A12 concentration-kinase activity curves.

Modeling studies were performed using the crystal structure coordinates of HCK (Sicheri et al., 1997, *Nature*, 385:602–9) and IRK (Hubbard, 1997, the *EMBO* Journal, 16:5572–5581) and constructed homology models for the kinase domains of JAK1, JAK3 ((Sudbeck et al., 1999, *Clin. Can. Res.* (in press)) and BTK (Mahajan et al., 1999, *JBC*, in press) to identify possible causes for the observed selectivity of LFM-A12 for the EGFR tyrosine kinase. While most of the catalytic site residues of the EGFR kinase domain were conserved realtive to other PTKs, we noted a few specific variatoins. EGFR residues Leu[694], Val[702], Lys[721], and Ala[719] are conserved in EGFR, HCK, FGFR and IRK. Residues Asn[818] and Asp[831] (opposite to hinge) are converved in EGFR, HCK, FGFR, IRK, BTK, JAK1 and JAK3. Residues Cys[751] and Thr[830] are specific for EGFR but vary in BTK (Val, Ser), JAK1 (Val, Gly), JAK3 (Val, Ala), IRK (Val, Gly), and HCK (Val, Ala). Residues Thr[766] and Leu[768] in the hinge region changes to Met and Leu in IRK, Met and Phe in JAK1, Met and Tyr in JAK3, and to Thr and Tyr in BTK. One region of the binding pocket contains Cys[773] in EGFR and is therefore considerably more hydrophobic than the corresponding residue of PDGFR (Asp), FGFR (Asn), JAK1 (Ser), HCK (Ser), and IRK (Asp).

Figure 6A:
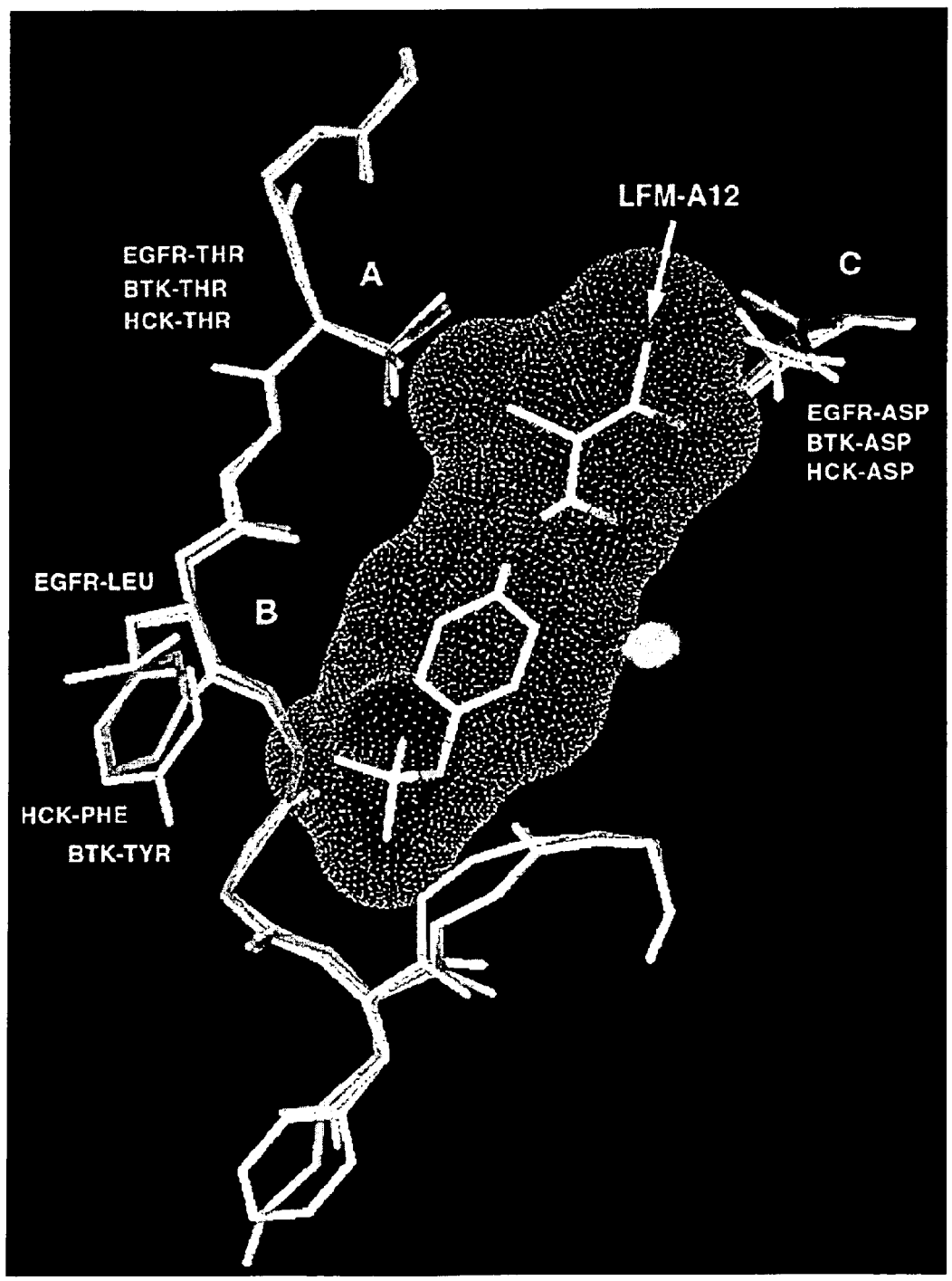
FIGS. 6A–6B show the docking of LFM-A12 and WHI-P154 into catalytic sites of kinases.

LFM-A12 was docked into the kinase domains of IRK, HCK, JAK3, JAK1, BTK and EGFR. After energy minimization the compound maintained favorable close contacts with the hinge region of each kinase although the orientation of LFM-A12 in the catalytic site was different for BTK and HCK as shown in FIG. 6A. When bindign with EGFR the inhibitor appeared to be sanwiched between four residus, Leu[694] and Val[702] from above and Leu[820] and Thr[830] from below. The nitrile nitrogen of the ligand was involved in hydrogen bonding with the amide NH of Met[769]. In addition, the para-substituted $OCF_3$ group on the lead compound appeared to form close contacts between residues Thr[766] and Asp[831] at positions A and C, respectively, of EGFR (FIG. 6B).

Table 3 shows the interaction scores, estimated $K_i$ values, and measured $IC_{50}$ data for LFM-A12 with the different kinases. The data indicated that the selectivity of LFM-A12 for EGFR likely results from its molecular shape and from favorable interactions with unique EGFR residues that are not present in the kinase domains of the other PTKs. Likewise, unfavorable interactions with unique residues of the other PTKs that are not found in the EGFR kinase domain also contribute to this selectivity. These residue differences are illustrated in FIGS. 6A and 6B at positions A and B.

FIG. 6A shows the backbone of the EGFR catalytic site, the residue differences between EGFR (white) and other kinases, and the docked position of LFM-A12 (multi-color) at this site in BTK (peach) which is also similar to the docked position in HCK (blue). FIG. 6B shows the docked position of LFM-A12 (multi-color) in EGFR (white), which is also similar to the docked position in JAK3 (pink) and IRK (green). The dotted surface area in each figure represents the Connolly surface of the inhibitor LFM-A12.

Figure 6B:
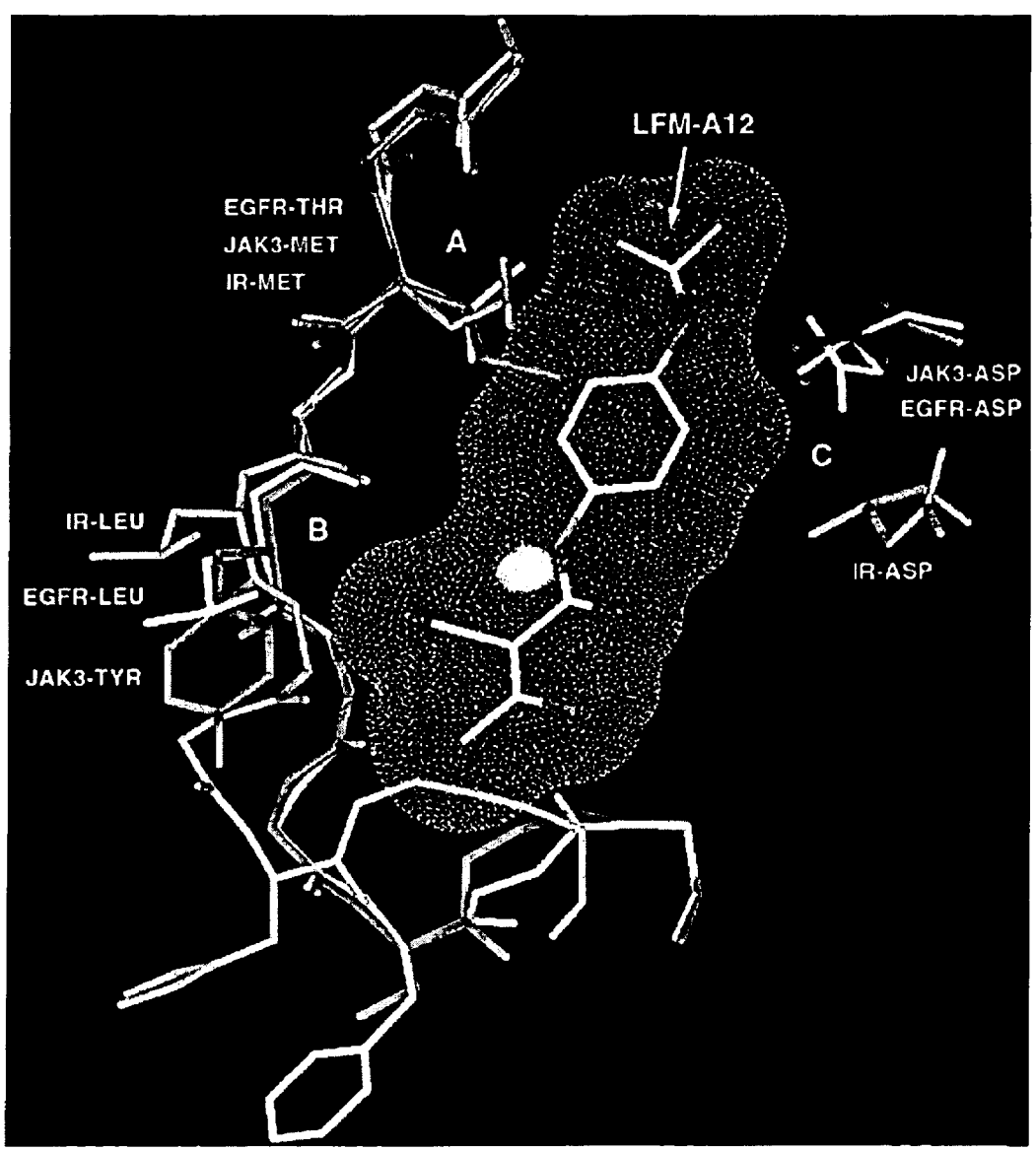

The aromatic residue in BTK (Tyr), HCK (Phe), JAK1 (Phe), JAK3 (Tyr) (shown at position B in FIGS. 6A and 6B, is not as favorable for interactions with the p-$OCF_3$ group of LFM-A12. The corresponding residue in the EGFR kinase domain is leucine (shown in white at position B in FIGS. 6A and 6B), which would not cause such unfavorable interactions with LFM-A12. Also, for HCK there is a loss of hydrogen bonding interaction with LFM-A12. Furthermore, JAK3, IRK (shown in FIG. 6B), and JAK1 (not shown) contain a methionine residue (at position A in FIG. 6B) which protrudes into the active site and could impair the close hydrophobic contact of LFM-A12 with the hinge region of the catalytic site. The longer methionine residue in JAK3 and IRK does not compliment the shape of LFM-A12 and may hinder its binding. As shown in FIG. 6B, the corresponding residue in the EGFR kinase domain is threonine (white); its relatively shorter side chain enables LFM- A12 (multicolor) to have a more favorable hydrophobic contact with the hinge region which may result in tighter binding to the EGFR binding site. For EGFR, the most active compound (LFM-A12) appears to be located between the residues at positions A and C. Consequently, the estimated $K_i$ value for the EGFR (13 $\mu$M) was lower than the $K_i$ values for other PTKs which ranged from 27 $\mu$M for BTK to 1710 $\mu$M for JAK3 (Table 3).

Confocal Imaging

The effects of LFM-A12 treatment on MDA-MB-231 cells were examined by confocal laser scanning microscopy. Slides were examined using a Bio-Rad MRC-1024 Laser Scanning Confocal Microscope mounted on a Nikon Eclipse E800 upright microscope with high numerical aperture objectives. Digital data was processed using Lasersharp (Bio-Rad, Hercules Calif.) and Adobe Photoshop software (Adobe Systems, Mountain View, Calif.) and printed on a Pictography printer (Fuji, Elmsford, N.Y.). Bohm, H. J. *J. Comput. Aided Mol. Des.*, 1994, 8, 243–256.

Figure 8A:
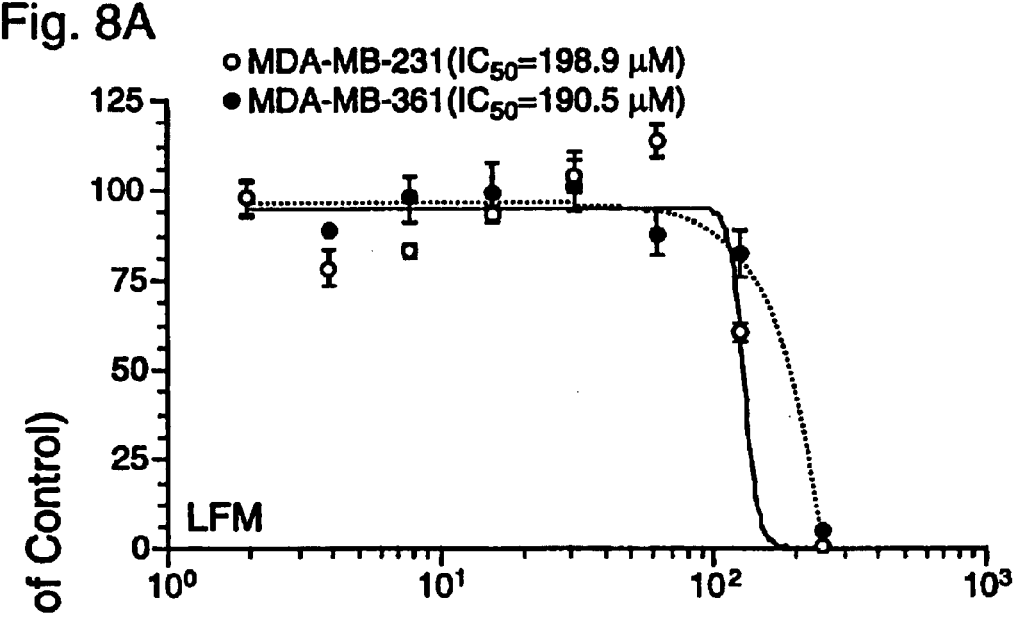
FIGS. 8A–8B are graphs showing the cytotoxic activity of LFM and LFM-A12 against human breast cancer cells in MTT assays. MDA-MB-231 and MDA-MB-361 cells were treated with LFM (FIG. 8A) or LFM-A12 (FIG. 8B) for 36 hours in 96-well plates and the cytotoxicity was determined by the MTT assay. The data points represent the mean (±SE) values from three independent experiments.
Figure 8B:
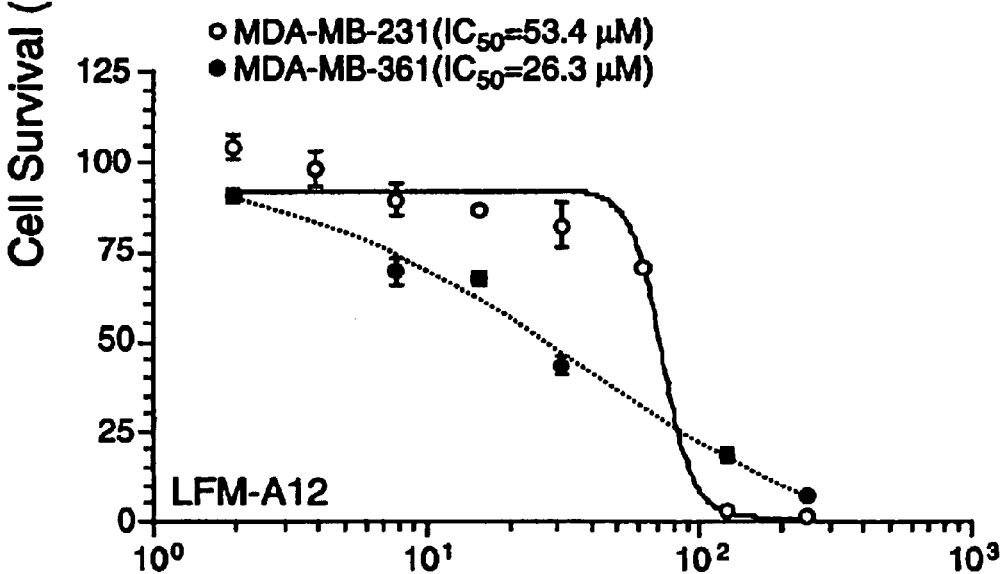

As shown in FIG. 8A, vehicle (DMSO) treated control cells were round and large with many well organized microtubules (green fluorescence secondary to tubulin staining) in the cytoplasm. Nuclei (blue fluorescence secondary to TOTO-3 staining) were also round and homogenous. In contrast, MDA-MB-231 cells treated with 100 $\mu$M LFM-A12 for 24 hours were much smaller and had an abnormal shape with large cytoplasmic vacuoles (FIG. 8B). The microtubules of LFM-A12 treated cells were fewer in number and they appeared less organized than those of DMSO treated controls. The nuclei (blue) of the LFM-A12 treated cells were also smaller and misshapen. Unlike LFM-A12, 100 EM LFM-A3 did not affect the morphology or microtubular organization of MDA-MB-231 cells (FIG. 8C).

Apoptosis Assays

The morphologic features of LFM-A12 treated MDA-MB-231 cells by immunocytohemistry (i.e., shrinkage, nuclear condensation, and abnormal microtubular organization) suggested that these cells might be undergoing apoptosis. Therefore, to determine whether LFM-A12 could trigger apoptosis in breast cancer cells, a quantitative flow cytometric apoptosis detection assay was performed.

Figure 9A:
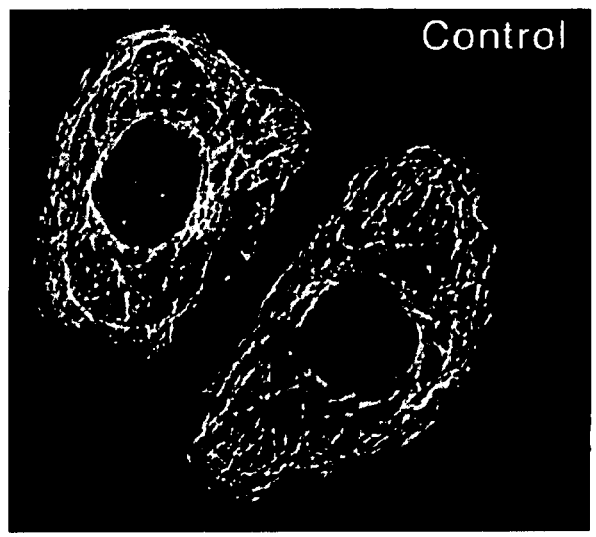
FIGS. 9A–9C are confocal images of LFM-A12—treated breast cancer cells. MDA B-231 cells were treated with LFM-A3 or LFM-A12 at a final concentration of 100 $\mu$M for 24 hours at 37° C., as described in the Examples. After treatment, cells were processed for immunofluorescence using a monoclonal antibody to α-tubulin (green fluorescence). LFM-A12 (FIG. 9A) but not LFM-A3 (FIG. 9C)—treated cells showed marked shrinkage with disruption of microtubules and lost their ability to adhere to the substratum. Blue fluorescence represents nuclei stained with TOTO-3. The control is shown in FIG. 9A FIGS. 10A and 10B diagramatically show regions of LFM-A12 suitable for modificatin to enhance EGFR inhibition. Structural and chemical features of LFM analogs which are proposed to aid binding to the EGFR catalytic site and are described below and illustrated. Binding Mode 1, (FIG. 10A) shows the most likely mode of binding of the lead compound LFM-A12 at the EGFR catalytic site. Based on the modifications of the lead compound, a second mode may also be possible and this is illustrated in FIG. 10B (Binding Mode 2).
Figure 9B:
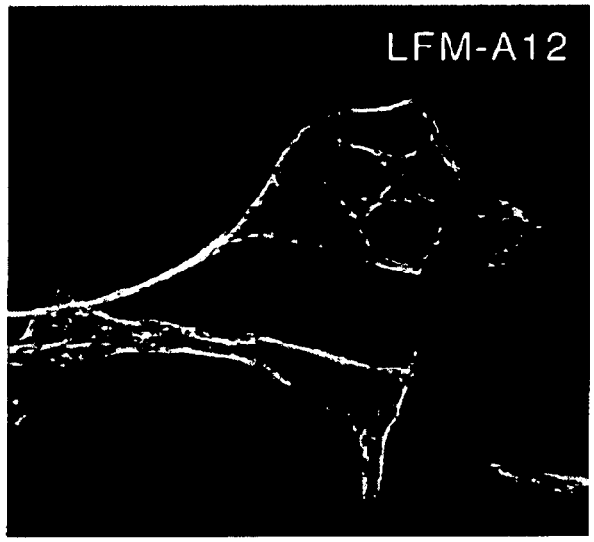
Figure 9C:
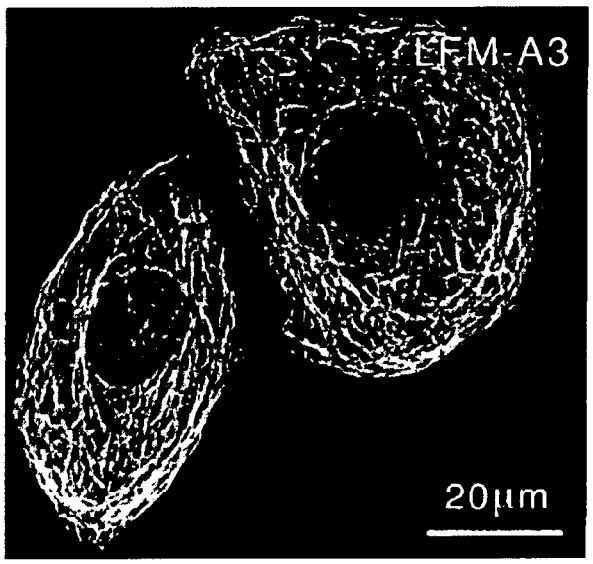

Loose packing of membrane phospholipid head groups and cell shrinkage precede DNA fragmentation in apoptotic cells, thereby providing MC540 binding as an early marker for apoptosis (Uckun, F. M. et al., *Science*, 1995, 267, 886–891). MC540 binding and propidium iodide (PI) permeability of MDA-MB-231 breast cancer cells were simultaneously measured before and after a 24 hour treatment with 100 $\mu$M or 500 $\mu$M LFM-A12. Whole cells were analyzed with a FACStar Plus flow cytometer (Becton Dickinson, San Jose, Calif.). Whereas less than 5% of MDA-MB-231 cells showed apoptotic changes after DMSO treatment, a significant portion of cells underwent apoptosis within 24 hours after LFM-A12 treatment (Apoptotic fraction [AF] with MC540$^+$/PI$^+$ advanced stage apoptosis: 54% at 100 $\mu$M and 85% at 500 $\mu$M) (FIG. 9). LFM, albeit to a lesser extent, also induced apoptosis in MDA-MB-231 cells.

Clonogenic Assays

The anti-cancer activity of LFM and LFM-A12 against MDA-MB-361 and MDA-B-231 breast cancer cells was tested using in vitro clonogenic assays. As shown in Table 4, 24 hour treatment with LFM or LFM-A12 inhibited the clonogenic growth of MDA-MB-361 cells as well as MDA-MB-231 cells in a dose-dependent fashion. At 100 $\mu$M, our lead compound LFM-A12 killed 87.3% of clonogenic MDA-MB-361 cells and >99% of clonogenic MDA-MB-231 cells.

TABLE 4

In Vitro Anti-Tumor Activity of LFM and LFM-A12 Against Clonogenic Breast Cancer Cells

| Cell Line | Treatment | Tumor Cell Colonies/$10^5$ Cells | % Inhibition |
|---|---|---|---|
| MDA-MB-361 | None | 1104 (924, 1284) | 0 |
|  | DMSO (0.1%) | 1088 (872, 1304) | 1.4 |
|  | LFM |  |  |
|  | 0.1 $\mu$M | 803 (702, 904) | 27.3 |
|  | 10 $\mu$M | 535 (386, 684) | 51.5 |
|  | 100 $\mu$M | 196 (128, 264) | 82.3 |
|  | LFM-A12 |  |  |
|  | 0.1 $\mu$M | 746 (316, 1276) | 32.4 |
|  | 10 $\mu$M | 440 (276, 604) | 60.2 |
|  | 100 $\mu$M | 140 (58, 222) | 87.3 |
| MDA-MB-231 | None | 1150 (1096, 1204) | 0 |
|  | DMSO (0.1%) | 953 (888, 1018) | 17.1 |
|  | LFM |  |  |
|  | 0.1 $\mu$M | 964 (588, 1340) | 16.2 |
|  | 10 $\mu$M | 642 (572, 712) | 44.2 |
|  | 100 $\mu$M | 297 (170, 424) | 74.2 |
|  | LFM-A12 |  |  |
|  | 0.1 $\mu$M | 667 (454, 880) | 42.0 |
|  | 10 $\mu$M | 515 (420, 610) | 55.2 |
|  | 100 $\mu$M | 0 | >99 |

Figure 7A:
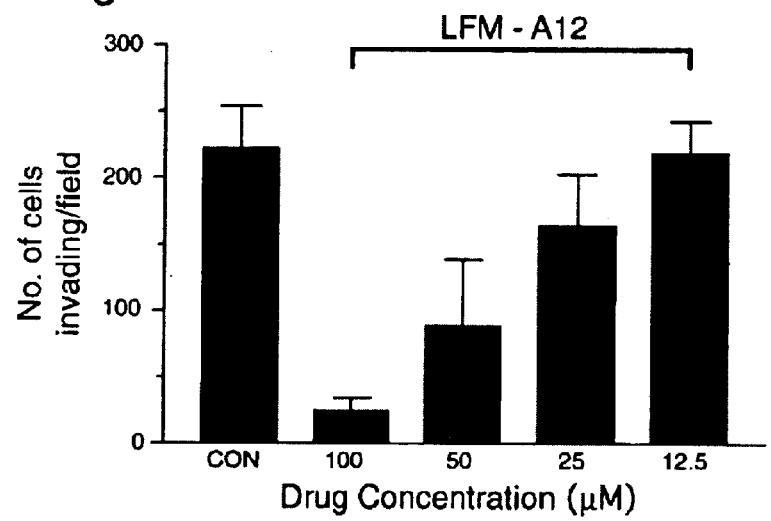
FIGS. 7A–7B demonstrates anti-invasive activity of LFM-A12 against MDA-MB-231 human breast cancer cells. Cells were incubated with the indicated concentrations of LFM or LFM-A12 for 24 hours, trypsinized, and placed in Boyden chambers precoated with Matrigel matrix and allowed to migrate for 48 hours. The migrated cells were stained with Hema II solution and counted. The data points are the mean values from two independent experiments. Untreated breast cancer cells were highly invasive in Matrigel-coated Boyden chambers.
Figure 7B:
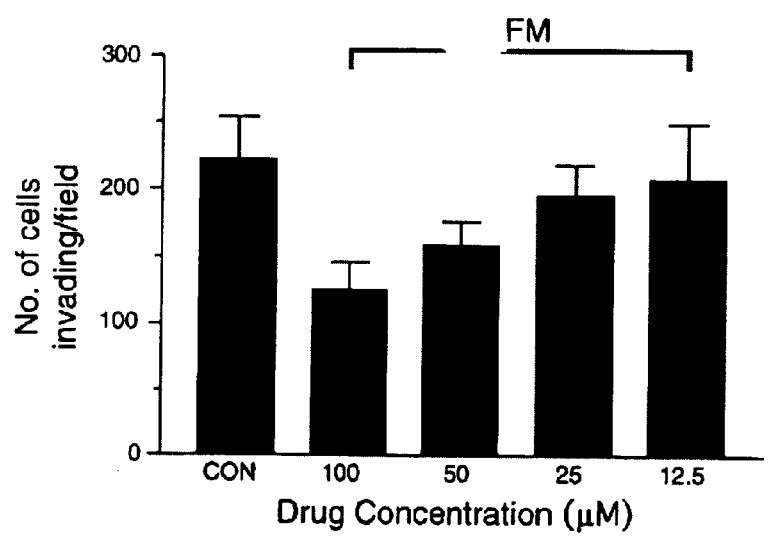
Figure 7B:

Effects of LFM-A12 on MDA-MB-231 Breast Cancer Cell Invasion Through Matrigel Matrix:

Matrigel matrix is made up of growth factors and several extracellular matrix (ECM) components, including collagens, laminin and proteoglycans. As shown in FIGS. 7A and 7B, MDA-MB-231 human breast cancer cells were highly invasive in Matrigel-coated Boyden chamber (CON). LFM-At2 inhibited the invasion of MDA-MB-231 cells through the Matrigel matrix in a dose-dependent fashion with an $IC_{50}$ value of 28.4 $\mu$M and it was more potent than LFM which had $IC_{50}$ value of 97.0 FM (FIGS. 7A and 7B).

EXAMPLE 6

Design of New Analogs

Exploring the Catalytic Site of EGFR for the Design of Specific Inhibitors

The binding volume of the EGFR catalytic site is much larger than the volume occupied by the lead compound LFM-A12. Increasing the size of the ligand is postulated to increase the contact area between the receptor and ligand and hence enhance binding.

Structural and chemical features of LFM analogs which aid binding to the EGFR catalytic site are described below and illustrated in FIGS. 10–11. Table 5 shows the residue differences at the ATP binding site between the six PTK's: EGFR, Btk, Hck, Jak1, Jak3 and IR.

TABLE 5

Residue differences between EGFR, Btk, Hck, Jak1, Jak3 and IR at the ATP binding pocket.

| No | EGFR | Btk | Jak1 | Jak3 | IR | Hck |
|---|---|---|---|---|---|---|
| 1 | Cys 751 | Val | Val | Val | Val | Val |
| 2 | Leu 764 | Ile | Leu | Leu | Val | Ile |
| 3 | Thr 766 | Thr | Met | Met | Met | Thr |
| 4 | Leu 768 | Tyr | Phe | Tyr | Leu | Phe |
| 5 | Cys 773 | Cys | Ser | Cys | Asp | Ser |

TABLE 5-continued

Residue differences between EGFR, Btk, Hck, Jak1, Jak3 and IR at the ATP binding pocket.

| No | EGFR | Btk | Jak1 | Jak3 | IR | Hck |
|----|------|-----|------|------|-----|-----|
| 6 | Arg 817 | Arg | Arg | Arg | Arg | Ala |
| 7 | Thr 830 | Ser | Gly | Ala | Gly | Ala |

T830, C751, T766, L764, L768, C773, R817 are some selected residues of the EGFR ATP binding site. Some or all of these residues are different from the ATP binding site of Btk, IR, Jak1, Jak3 and Hck. Amongst them, the residues Thr830 and Cys751 are specific for EGFR. These nonconserved residues can be utilized for the design of more potent and selective inhibitors of EGFR. In particular, targeting these residues for interaction with specific inhibitor moieties would impact the binding and stability of the inhibitor in the binding pocket, and enhance the specificity of the inhibitor for EGFR.

Listed in Table 6 are some groups which are proposed to aid binding to the EGFR catalytic domain, for example by providing favorable groups for interaction with the EGFR kinase active site.

TABLE 6

Substitutions on LFM analogs likely to increase the binding affinity for EGFR.

| No | Targeting | Effect | Substitutions |
|----|-----------|--------|---------------|
| 1 | Cys 751 | would increase the specificity for EGFR | Hydrophobic groups reaching about 5.5 Å down from para-O |
| 2 | Leu 764 | would not interact with Btk, IR and Hck | Small hydrophobic groups approximately within 3 Å from para-O |
| 3 | Thr 766 | would not interact with Jak1, Jak3 and IR | Small hydrogen bonding groups approximately within 3 Å from ortho and meta positions of ring (facing hinge). |
| 4 | Leu 768 | | |
| 5 | Cys 773 | would not interact with Jak1 and IR. | Hydrophobic groups reaching about 3.0 Å down from OH group of ligand |
| 6 | Arg 817 | would not interact with Hck | Long chain charged group stretching about 7.0–8.0 Å from OH or O group of ligand. |
| 7 | Thr 830 | would increase the specificity for EGFR | Hydrophobic groups reaching approximately 3.5 Å down from ortho and meta positions of ring (opposite hinge). |

Figure 10A:
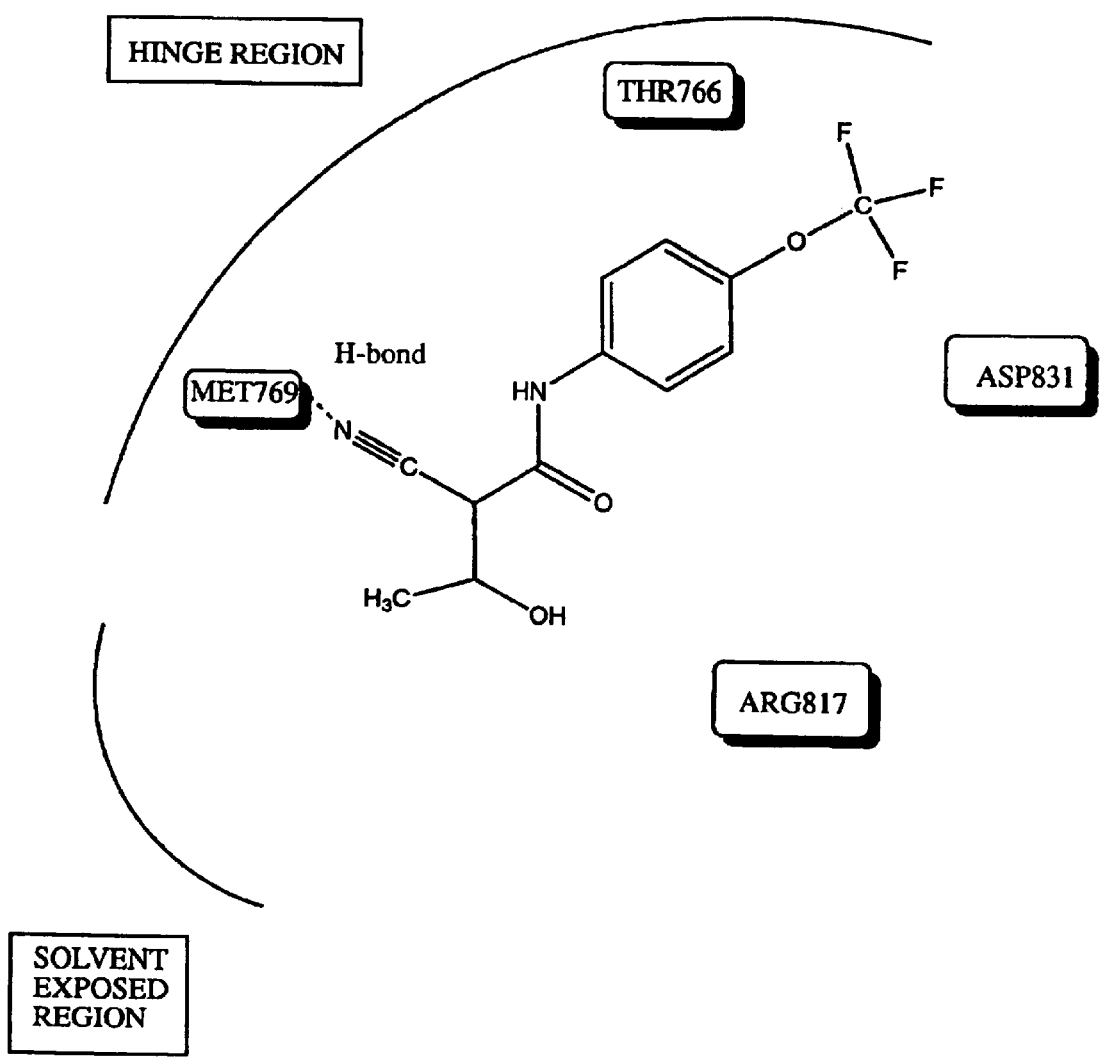
Figure 10B:
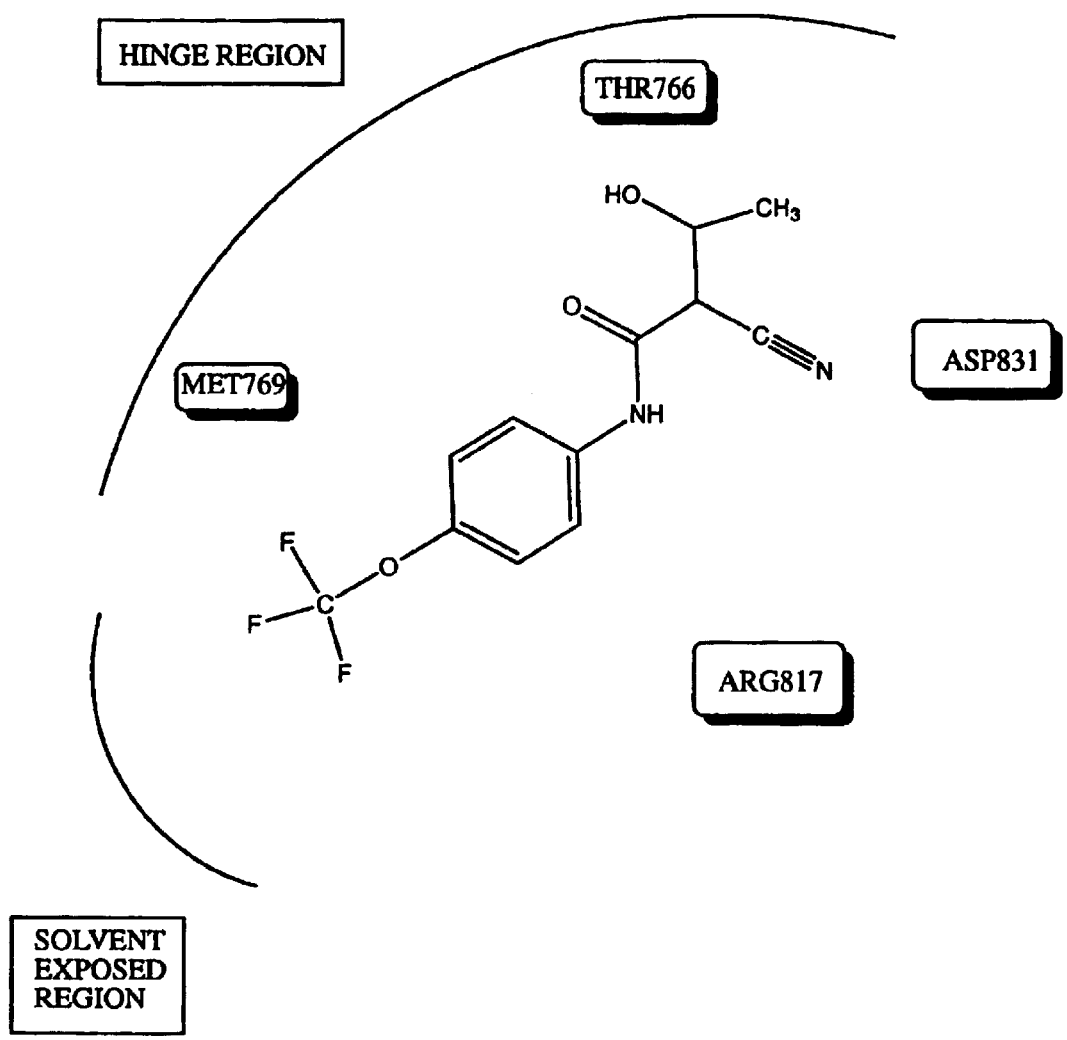

Referring to FIG. 10A, the lead compound LFM-A12 is shown bound to the EGFR-kinase domain in the predicted binding mode. A second possible bindign mode is shown in FIG. 10B. Our modeling studies indicate that para substituted compounds maintain good contact with the hinge region fo the receptor and appear to be good inhibitors by our calculations. For the para substituted compounds, a second mode of binding may also be possibly where the molecule is roated 180° such that the aromatic ring is near residues P770, F771, G772, and the chain is new residues L764, T766, D831 (FIG. 10B).

In order to increase the affinity and specificity of the existing ligang (LFM-Al2), more ineractions with the active site residues are desired. Substitutions at positions $R_1$ and $R_6$–$R_7$ of formula II are expected to lead to increased binding affinity at the catalytic site of EGFR. This expectation is based on the observation that the catalytic site of the EGFR kinase domain is much larger (volumne of about 500 Å$^3$) than the volue occupied by our most potent compounds. Increasing the size of the ligand, preferably to fill up to about ⅔ of the volume (about 400 Å$^3$) is predicted to increase the contact area between the receptor and ligand and thus enhance binding.

The designed compounds of formulae III–VI are expected to provide such increased contact with the receptor, have enhanced binding, and potent inhibitory activity.

Novel compounds designed to fit and interact with specific contact points of the EGFR-TK binding pocket have the following structural formulae (III–VI):

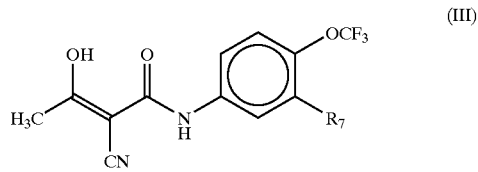
(III)

where $R_5$ is H, $NH_2$, $CH_3$, OH, $CF_3$, or halo. Preferably, $R_5$ is not H, and halo is Br or Cl.

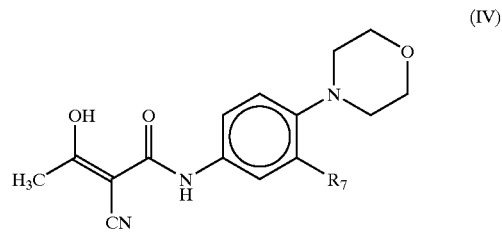
(IV)

where $R_5$ is H, $NH_2$, $CH_3$, OH, $CF_3$, or halo. Preferably, $R_5$ is not H, and halo is F or Cl.

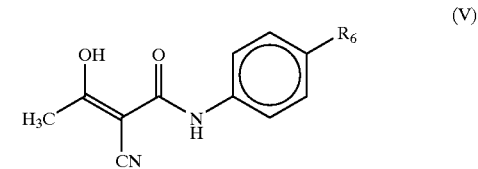
(V)

where $R_4$ is NH—$CH_3$ or $OCH_3$.

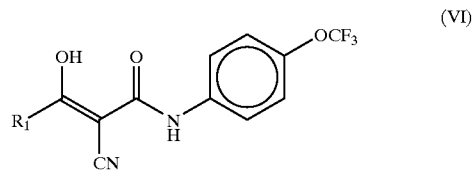
(VI)

where $R_1$ is —$CH_2$—$CH_2$X and X is halo, preferably Cl or Br; or $R_1$ —$^{CH}_2CF_3$; or $R_1$ is:

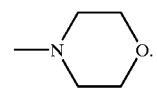

These compounds are synthesized as detailed in the following schemes, according to their type of modifications. By using the proper substituted-aniline, the compounds shown as formulae III, IV, and V may be synthesized by the same general synthetic pathway used above for Example 4 (Scheme 1). Synthetically, the entry for synthesizing the compounds of formula VI is to use different acylating agent, acid chloride, in the last step of the synthetic pathway shown in Scheme 1. The following schemes illustrate the four general types of modifications, and general synthesis schemes for the desired substituted-analines for the four types.

Scheme 3:
Synthesis of the Desired Substituted-Anilines for Type I Modification (Compounds of Formula III)

Scheme 3 illustrates a strategy for the synthesis of the desired substituted-analines for Type-I modification. All the starting materials used in Scheme 3 are commercially available.

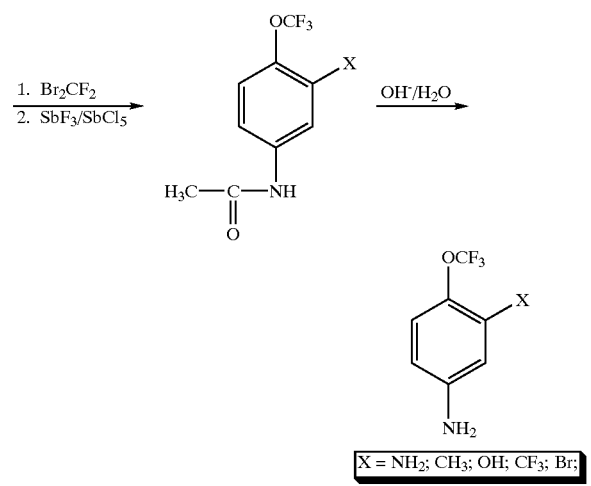

Scheme 4:
Synthesis of the Desired Substituted-Analines for Type II Modification (Compounds of Formula IV)

Scheme 4 is one approach to synthesizing all the needed substituted-analines for Type-II modification, e.g., the production of compounds of formula V. All the starting material used in Scheme 4 are commercially available.

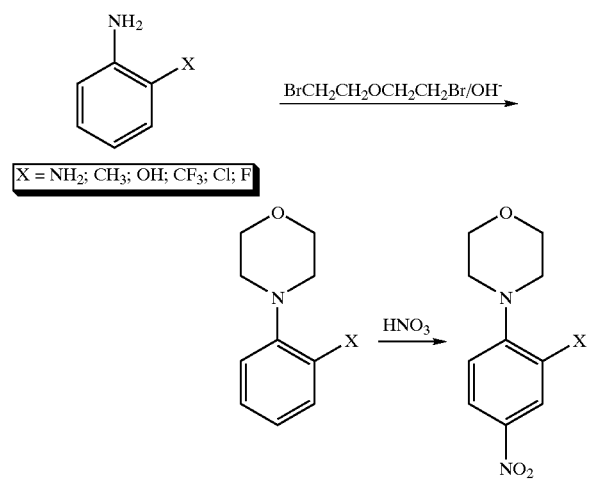

Scheme 5:
Synthesis of the Desired Substituted-Analines for Type III Modification (Compounds of Formula V)

For type III modification, producing compounds of formula VI, the starting substituted-analine for synthesizing the compound of $R_3$=—OCH, is commercially available. The starting material for synthesizing the compound of $R^3$=—NH—CH3 is shown in Scheme 5.

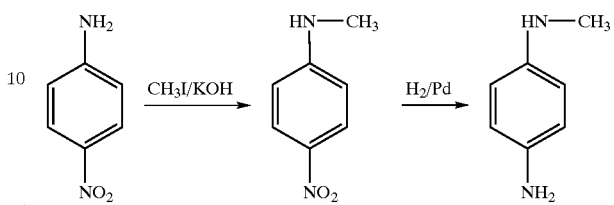

Scheme 6:

The Desired Acid Chlorides for Type IV Modification (Compounds of Formula VI)

For the type IV modification, to produce the compounds of formula VII, the desired acid chlorides, 4-morpholinecarbonyl chloride (4), mehtyl chloroforunate, (5), methyl chlorothioformate (6), trifluoroacetyl chloride (7), as shown in Scheme 6, are commercially available.

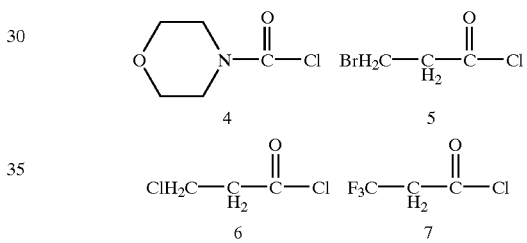

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A method for inhibiting EGFR tyrosine kinase, the method comprising contacting the EGFR with a compound having the structural formula:

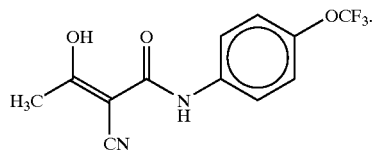

2. A method for inhibiting EGFR tyrosine kinase without inhibiting Src family tyrosine kinases, Tec family tyrosine kinases, or Janus family tyrosine kinases, the method comprising contacting the EGFR with a compound having the structural formula:

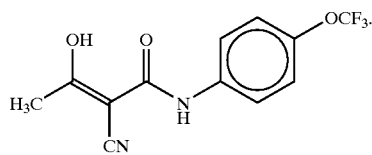
3. A method of treating cancer cells that express EGFR, the method comprising contacting the cancer cells that express EGPR with a compound having the structural formula:
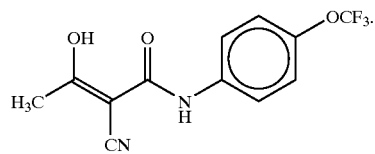
* * * * *